US009920356B2

(12) United States Patent
Takahashi et al.

(10) Patent No.: US 9,920,356 B2
(45) Date of Patent: Mar. 20, 2018

(54) AMPLIFIED NUCLEIC ACID DETECTION METHOD AND DETECTION DEVICE

(75) Inventors: Koji Takahashi, Takasago (JP); Shigehiko Miyamoto, Takasago (JP); Takaaki Jikihara, Takasago (JP); Jun Tomono, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 13/989,207

(22) PCT Filed: Nov. 24, 2011

(86) PCT No.: PCT/JP2011/077050
§ 371 (c)(1),
(2), (4) Date: Aug. 9, 2013

(87) PCT Pub. No.: WO2012/070618
PCT Pub. Date: May 31, 2012

(65) Prior Publication Data
US 2014/0065725 A1    Mar. 6, 2014

(30) Foreign Application Priority Data

Nov. 24, 2010 (JP) .................. 2010-261728
Jun. 28, 2011 (JP) .................. 2011-143424

(51) Int. Cl.
C12P 19/34    (2006.01)
C12Q 1/68     (2006.01)
(Continued)

(52) U.S. Cl.
CPC ........... *C12Q 1/6834* (2013.01); *C12Q 1/686* (2013.01); *G01N 33/54313* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS 5,310,650 A        5/1994  McMahon et al.
5,475,098 A  *    12/1995  Hall ....................... C12Q 1/689
                                                                 530/324
(Continued)

FOREIGN PATENT DOCUMENTS

CN    1459506 A    12/2003
CN    1697883 A    11/2005
(Continued)

OTHER PUBLICATIONS

Bindon et al., Nucleic Acids Research, 26, 3305-3308, 1998.*
(Continued)

*Primary Examiner* — Frank Lu
(74) *Attorney, Agent, or Firm* — Polsinelli PC

(57) ABSTRACT

An object of the invention is to provide a nucleic acid detection method which takes advantage of the high specificity of hybridization techniques, reduces the time length and the number of steps required for detection of PCR products, and allows for easy and highly accurate detection by visual observation without the need of special equipment; and a nucleic acid detection device or kit. The invention provides a method for detecting a target nucleic acid in a sample, which includes performing amplification of the target nucleic acid sequence to synthesize an amplification product having a partially double-stranded structure where a single-stranded region is added to each end of the target sequence, and hybridizing a nucleic acid sequence bound to a development medium and a nucleic acid sequence labeled with a labeling compound with the single-stranded regions of the amplification product to form a sandwich hybridization complex; and a detection device thereof.

13 Claims, 3 Drawing Sheets

(51) Int. Cl.
C07H 21/02 (2006.01)
C07H 21/04 (2006.01)
C07H 21/00 (2006.01)
G01N 33/543 (2006.01)

(56) References Cited

U.S. PATENT DOCUMENTS

| | | | |
|---|---|---|---|
| 5,525,494 | A | 6/1996 | Newton |
| 5,629,158 | A * | 5/1997 | Uhlen .................. C12Q 1/6834 435/6.14 |
| 5,874,216 | A * | 2/1999 | Mapes .......................... 435/6.11 |
| 7,932,060 | B2 * | 4/2011 | Nadeau ................ C12Q 1/6851 435/6.1 |
| 2003/0108913 | A1 * | 6/2003 | Schouten ............... C12Q 1/686 435/6.18 |
| 2005/0142559 | A1 | 6/2005 | Makrigiorgos |
| 2006/0134802 | A1 * | 6/2006 | Donati ................. G01N 33/558 436/514 |
| 2008/0274464 | A1 | 11/2008 | Goto et al. |
| 2009/0047673 | A1 | 2/2009 | Cary |
| 2009/0136956 | A1 | 5/2009 | Merante et al. |
| 2010/0291666 | A1 | 11/2010 | Collier et al. |
| 2010/0330564 | A1 | 12/2010 | Tomono |
| 2010/0330574 | A1 | 12/2010 | Whitman et al. |
| 2011/0244597 | A1 | 10/2011 | Tsukada et al. |
| 2012/0053063 | A1 * | 3/2012 | Rigatti et al. ..................... 506/2 |
| 2013/0052652 | A1 | 2/2013 | Schneider et al. |
| 2014/0065725 | A1 | 3/2014 | Takahashi et al. |

FOREIGN PATENT DOCUMENTS

| | | |
|---|---|---|
| CN | 1891832 A | 1/2007 |
| CN | 1982325 A | 6/2007 |
| CN | 101137759 A | 3/2008 |
| CN | 101845511 A | 9/2010 |
| EP | 0416817 A2 | 3/1991 |
| EP | 1634962 A1 | 3/2006 |
| EP | 2410063 A1 | 1/2012 |
| EP | 2762562 A1 | 8/2014 |
| EP | 2789689 A1 | 10/2014 |
| JP | H02-283299 A | 11/1990 |
| JP | H02283299 A | 11/1990 |
| JP | 03-272686 A | 4/1991 |
| JP | 03-272686 B2 | 4/1991 |
| JP | H03-272686 A | 12/1991 |
| JP | 05-252998 A | 5/1993 |
| JP | 2001157598 A | 6/2001 |
| JP | 2002-530677 A | 9/2002 |
| JP | 2002-534434 A | 10/2002 |
| JP | 2003-504018 A | 2/2003 |
| JP | 2004-502464 A | 1/2004 |
| JP | 2006-201062 A | 8/2006 |
| JP | 2006-524993 A | 11/2006 |
| JP | 2007-111048 A | 5/2007 |
| JP | 2007-526443 A | 9/2007 |
| JP | 2008-525037 A | 7/2008 |
| JP | 2009-521924 A | 6/2009 |
| JP | 2009-162535 A | 7/2009 |
| JP | 2009-296948 A | 12/2009 |
| JP | 2010-014507 A | 1/2010 |
| JP | 2010-513854 A | 4/2010 |
| WO | WO-1996/36733 A1 | 11/1996 |
| WO | WO-98/14610 A2 | 4/1998 |
| WO | WO-00/31539 A1 | 6/2000 |
| WO | WO-0040592 A1 | 7/2000 |
| WO | WO-2001/02559 A1 | 1/2001 |
| WO | WO-2001/21637 A1 | 3/2001 |
| WO | WO-2002/004668 A2 | 1/2002 |
| WO | WO-2002024944 A2 | 3/2002 |
| WO | WO-2004/099438 | 11/2004 |
| WO | WO-2004/109285 A1 | 12/2004 |
| WO | WO-2006/071770 A2 | 7/2006 |
| WO | WO-2006/095550 A1 | 9/2006 |
| WO | WO-2006/043387 A1 | 5/2008 |
| WO | WO-2008/075213 A2 | 6/2008 |
| WO | WO-2009//034842 A1 | 3/2009 |
| WO | WO-2010/061772 A1 | 6/2010 |
| WO | WO-2010106997 A1 | 9/2010 |
| WO | WO-2011-137911 A2 | 11/2011 |
| WO | WO-2012070618 A1 | 5/2012 |
| WO | WO-2013-040491 A2 | 3/2013 |
| WO | WO-2013038534 A1 | 3/2013 |
| WO | WO-2013039228 A1 | 3/2013 |

OTHER PUBLICATIONS

International Preliminary Report on Patentability dated Jun. 12, 2013 in Appl. No. PCT/JP2011/077050.
Jung et al., "Fabrication of single-walled carbon nanotubes dotted with Au nanocrystals: Potential DNA delivery nanocarriers", Carbon, vol. 48, No. 4, 2010, pp. 1070-1078, XP026859548.
Liang et al., "Construction of a photo-switchable gene for turning on and off gene expression with light irradiation", Nucleic Acids Symposium Series, vol. 52, 2008, pp. 19-20, XP002721990.
Reinhartz, et al., "A novel rapid hybridization technique: paper chromatography hybridization assay (PACHA)", Gene, vol. 136, No. 1-2, 1993, pp. 221-226, XP023797207.
Highlighting Japan Online Magazine, "Easy Detection of Mutiple Genes", [Series] Science & Technology, Mar. 2013, XP002721991.
Newton et al., "The production of PCR products with 5' single-stranded tails using primers that incorporate novel phosphoramidite intermediates", Nucleic Acids Research, 1993, vol. 21, No. 5, 1155-1162.
Corstjens et al., "Lateral-flow and up-converting phosphor reporters to detect single-stranded nucleic acids in a sandwich-hybridization assay", Analytical biochemistry, 312 (2003) 191-200.
Vircell, Speed-oligo Informative Dossier (the second edition), Jun. 2010.
Jusus de la Calle I. et al., 19th European Congress of Clinical Microbiology and Infectious Diseases, May 2009.
Yoshinao Wada, "Separate Analysis of Complementary Strands of Restriction Enzyme-digested DNA. An Application of Restriction Fragment Mass Mapping by Matrix-assisted Laser Desorption/Ionization Mass Spectrometry", Journal of Mass Spectrometry, vol. 33, pp. 187-192 (1998).
Kaluz et al., "Ligation-independent cloning of PCR products with primers containing nonbase residues", Nucleic Acids Research, 1994, vol. 22 No. 22, p. 4845.
Hayashi et al., (Application of L-DNA as a molecular tag. Nucleic Acids Symp Ser (Sep. 2005) 49 (1):261-262).
Hauser et al., (Utilising the lest-helical conformation of L-DNA for analysing different marker types on a single universal microarray platform, Nucleic Acids Res. Oct. 2006; 34(18): 5101-5111. Published online Sep. 20, 2006).
Liang et al., "Nick Sealing by T4 DNA Ligase on a Modified DNA Template: Tethering a Functional Molecule on D-Threoninol", Chem. Eur. J., 2011, vol. 17, pp. 10388-10396.
International Preliminary Report on Patentability dated Oct. 28, 2014 in PCT/JP2013/062488.
Preceedings, The 77th Annual Meeting of the Chemical Society of Japan, Union of Chemistry-Related Societies Research Workshop, Sep. 10, 1999, p. 229.
Asanuma et al., "Photo-Responsive Oligonucleotides Carrying Azobenzene in the Side-Chains", Tetrahedron Letters, vol. 39, No. 49, pp. 9015-9018.
English abstract for Journal of Synthetic Organic Chemistry, Japan, 2005, vol. 63, pp. 63-75.
Yamazawa et al., "Photoregulation of the DNA Polymerase Reaction by Oligonucleotides Bearing an Azobenzene", Angew. Chem. Int. Ed., 2000, 39, No. 13, 2356-2357.
Yamazawa et al., Supporting Information n-Supplemental Figure 1-3, Agnew. Chem. 2000.
Carter et al., "Lateral flow microarrays: a novel platform for rapid nucleic acid detection based on miniaturized lateral flow chromatography", Nucleic Acids Research, 2007, vol. 35, No. 10 (e74, Epub May 3, 2007).

(56) References Cited

OTHER PUBLICATIONS

Liu et al., "A universal biosensor for multiplex DNA detection based on hairpin probe assisted cascade signal amplification", Chem Commun., 2013, 49, 5165-5167.
Takeshi Ujiiye, "Useful Method Nucleic Acid-Chromatography for genetic testing", Clinical Chemistry, vol. 36, 2007, pp. 19-24 (Partial Translation).
Brownie et al., "The elimination of primer-dimer accumulation in PCR", Nucleic Acids Res., Aug. 15, 1997, (25(16): 3235-3241.
Oku et al., "Development of oligonucleotide lateral-flow immunoassay for multi-parameter detection", Journal of Immunological Methods, 258 (2001) 73-84.
Shimizu et al., "Evaluation of Immunochromatography Based Rapid Detection Kit of Rotavirus and Adenovirus", The Journal of the Japanese Association for Infectious Diseases, vol. 75 No. 12, pp. 1040-1046, 2001.
DIPSTICK 'Eiken' ADENO, Aug. 2008.
DIPSTICK 'Eiken' ROTA, Apr. 2008.

* cited by examiner

AMPLIFIED NUCLEIC ACID DETECTION METHOD AND DETECTION DEVICE

CROSS REFERENCE TO RELATED APPLICATIONS

This application is a National Phase filing under 35 U.S.C. § 371 of PCT/JP2011/077050 filed on Nov. 24, 2011; and this application claims priority to Application No. 2010-261728 filed in Japan on Nov. 24, 2010, and Application No. 2011-143424 filed in Japan on Jun. 28, 2011, under 35 U.S.C. § 119; the entire contents of all are hereby incorporated by reference.

TECHNICAL FIELD

The present invention relates to a simple method for detecting amplified nucleic acids and a device for use in the method.

BACKGROUND ART

Techniques for specifically amplifying a target nucleic acid sequence are very important for research and clinical applications (e.g. genetic testing) in molecular biology. An amplification product obtained by such a nucleic acid amplification technique can be specifically detected, for example, by a detection method using a target sequence-containing nucleic acid fragment immobilized on a solid phase. This method, which is designed to specifically capture a target nucleic acid on the solid phase, allows for easy removal of non-specific nucleic acids by washing or the like, and thus improves the detection specificity.

In this method, in order to capture a target nucleic acid on the solid phase, a technique using an antigen-antibody or ligand-receptor pair capable of specifically binding together may be used. For example, Non Patent Literature 1 discloses a method for detecting a product of PCR amplification using a primer terminally modified with biotin and another primer modified with a fluorescent substance. In this method, the PCR product is contacted with a solid phase containing streptavidin and agarose, and then bonded to the solid phase as a streptavidin-biotin complex, which can be measured for fluorescence to assay the target amplification product.

Unfortunately, the number of antigen-antibody or ligand-receptor combinations usable for labeling is limited, which makes it substantially difficult to simultaneously detect multiple target nucleic acids. Another problem is the cost: fluorescently labeled nucleic acids are expensive.

Another technique for capturing a target nucleic acid on a solid phase is to immobilize a probe containing an oligonucleotide having a complementary sequence to the target nucleic acid on the solid phase, which enables the target nucleic acid to be indirectly immobilized on the solid phase through hybridization of the target nucleic acid and the probe. This technique is accompanied with detection of the intensity of a signal of the formed hybrid. This type of nucleic acid analysis makes it possible to simultaneously assay multiple target sequences by using varied probe sequences.

In general, however, hybridization of an immobilized probe and a target nucleic acid on a solid phase requires heating treatment for denaturing a double-stranded nucleic acid amplified by PCR into single strands. Unfortunately, this heating treatment is troublesome and is also associated with a reduction in hybridization efficiency due to reannealing. Another problem is that single-stranded DNA tends to curl into a ball and is thus inferior in detection sensitivity. Although Patent Literature 1 discloses a technique for amplifying a single-stranded nucleic acid via nuclease treatment without heating treatment, this technique is also a troublesome procedure and has the problem of curling of single strands into balls.

Among nucleic acid detection methods, the method based on chromatography disclosed in Patent Literature 2 is easy to operate and allows for rapid and easy detection of target nucleic acids. This is a gene detection method that includes the steps of sampling genes from a cell, virus or bacterium, fragmenting the randomly sampled genes, and detecting a target gene, wherein these steps are continuously performed on a single device for gene detection by transferring a liquid sample containing the randomly sampled genes or fragments thereof by capillary action. This method allows not only assessment of the presence of a target gene but also identification of its type.

Also in Patent Literature 2, however, single-stranded nucleic acids are amplified by NASBA. The problems in the use of single-stranded nucleic acids are as described above.

In order to solve the above problems, Patent Literatures 3 and 4 disclose that a non-natural nucleic acid tag, a hairpin structure or a pseudoknot structure for inhibiting nucleic acid synthesis by DNA polymerase is present on the 5' side of the primer region. Thus the single-stranded region is left at one end of the double-stranded nucleic acid after PCR reactions. This technique is advantageous in that an amplified double-stranded DNA product having a hybridizable single-stranded region at one end of the double-stranded DNA can be produced only by performing PCR reactions using such a special primer. However, since a fluorescent label or surface plasmon resonance (SPR) imaging is required for detection, expensive special equipment is necessary. Additionally, there are problems with speed and simplicity.

CITATION LIST

Patent Literature

Patent Literature 1: JP-A H05-252998
Patent Literature 2: JP-A 2006-201062
Patent Literature 3: WO 2006/095550
Patent Literature 4: JP-A 2009-296948

Non Patent Literature

Non Patent Literature 1: Analytical biochemistry, 193, 231-235, (1991)

SUMMARY OF INVENTION

Technical Problem

Genetic diagnosis and genetic testing in clinical practice often impose the burdens of patient testing costs and several hospital visits because they require large-scale, expensive test equipment and take a long time for testing. Accordingly, there is a need for reducing the burdens on patients and testers without sacrificing the accuracy of testing, and thus simple, rapid, highly-specific, and low-cost methods that do not require special equipment are being sought. The present invention was made to solve the above problems, and an object of the present invention is to provide a nucleic acid detection method which takes advantage of the high specificity of hybridization techniques, reduces the time length and the number of steps required for detection of PCR products, and allows for easy and highly accurate detection by visual observation without the need of special equipment; and a nucleic acid detection device or kit. Meanwhile, conventional techniques leave room for improvement in terms of time and costs because they require the preparation of an expensive label tag for each target nucleic acid.

Solution to Problem

As a result of intensive studies to solve the above problems, the present inventors have independently found that it is possible to easily and accurately detect an amplified DNA fragment without the need of special equipment by amplifying the target nucleic acid in the form of a double-stranded nucleic acid having a single-stranded region at each end thereof, allowing the amplified fragment to bind to a solid phase with an oligonucleotide probe capable of hybridizing to one of the single-stranded regions, and detecting the binding. Thus, the present invention has been completed.

Specifically, the present invention relates to a nucleic acid detection method, including the step of hybridizing a first oligonucleotide probe immobilized on a solid phase with one of single-stranded regions which contain natural nucleotides and are respectively located at opposite ends of an amplified double-stranded DNA fragment.

Preferably, the method further includes the step of hybridizing a second oligonucleotide probe labeled with a labeling substance with the other single-stranded region of the amplified DNA fragment.

Preferably, the labeling substance includes a colored carrier that allows the amplified DNA fragment to be visually detected.

Preferably, the method includes the step of detecting the presence of the amplified DNA fragment on a nucleic acid detection device.

Preferably, the presence of the amplified DNA fragment is detected by chromatography.

Preferably, the method includes the following steps (a) to (c):

(a) placing the amplified DNA fragment in a zone on the nucleic acid detection device which is different from a zone where the first oligonucleotide probe is immobilized;

(b) diffusing the amplified DNA fragment with a solvent on the device toward the zone where the first oligonucleotide probe is immobilized; and (c) hybridizing the first oligonucleotide probe with the amplified DNA fragment in the zone where the first oligonucleotide probe is immobilized.

Preferably, the method further includes the step of hybridizing the second oligonucleotide probe labeled with the labeling substance with the amplified DNA fragment before the step (c).

Preferably, the method includes the following steps (d) to (h):

(d) placing the amplified DNA fragment and the second oligonucleotide probe labeled with the labeling substance respectively in discrete zones on the nucleic acid detection device which are different from a zone where the first oligonucleotide probe is immobilized;

(e) diffusing the amplified DNA fragment with a solvent toward the zone where the second oligonucleotide probe labeled with the labeling substance is placed;

(f) hybridizing the second oligonucleotide probe labeled with the labeling substance with the amplified DNA fragment in the zone where the second oligonucleotide probe labeled with the labeling substance is placed;

(g) diffusing a hybridization complex obtained in the step (f) on a development medium toward the zone where the first oligonucleotide probe is placed; and (h) hybridizing the first oligonucleotide probe with the complex in the zone where the first oligonucleotide probe is immobilized.

Preferably, each of the single-stranded regions containing natural nucleotides has a sequence in the same orientation as the double-stranded DNA region.

Preferably, the amplified DNA fragment is a product obtained by a nucleic acid amplification technique using two primers each containing a tag region that is not made double-stranded by a nucleic acid amplification reaction.

Preferably, the amplified DNA fragment is a product obtained by a nucleic acid amplification technique using a first primer set including primers each containing a sequence capable of hybridizing to a template of the target nucleic acid and a common sequence incapable of hybridizing to the template, and a second primer set including primers each containing a sequence capable of hybridizing to a complementary sequence to the corresponding common sequence and a tag region that is not made double-stranded by a nucleic acid amplification reaction.

Preferably, the tag region that is not made double-stranded by a nucleic acid amplification reaction contains natural nucleotides, and the entire sequences of each primer of the second primer set is in the same orientation.

The present invention also relates to a nucleic acid detection device for use in the nucleic acid detection method, which includes a zone where the amplified DNA fragment is placed; a chromatographic carrier having the first oligonucleotide probe capable of binding to the amplified DNA fragment; and the second oligonucleotide probe labeled with the labeling substance.

The present invention further relates to an amplified double-stranded DNA fragment which is produced by a nucleic acid amplification technique using two primers each containing a tag region that is not made double-stranded by a nucleic acid amplification reaction, and which has at each end thereof a single-stranded region containing natural nucleotides.

Preferably, the tag region of each primer that is not made double-stranded by a nucleic acid amplification reaction contains natural nucleotides, and the entire sequence of each primer is in the same orientation.

Advantageous Effects of Invention

The present invention allows an amplified DNA product to specifically bind to a solid phase via a single-stranded region of the amplified DNA product, and to form a complex with a labeling compound via the other single-stranded region thereof. This allows for easy and rapid detection of the amplified DNA product by visual observation without using special equipment. Additionally, the present invention, which involves detecting structurally stable double-stranded DNA, improves in detection sensitivity, compared to in the detection of entirely single-stranded sequences. Furthermore, two or more target nucleic acids in a sample can be assayed simultaneously by preparing multiple pairs of a single-stranded region of an amplification product to be bonded to the solid phase and an oligonucleotide probe on the solid phase that is complementary to that region. According to another embodiment of the present invention, it is possible to add a single kind of single-stranded region to any target nucleic acids through a low-cost joint primer. The use of a single kind of single-stranded region allows any detection to be carried out using a single kind of label tag and a single device. In this case, it is not necessary to prepare an expensive label tag for each target nucleic acid, which leads to a great improvement in terms of time and costs.

DESCRIPTION OF EMBODIMENTS

The present invention relates to a nucleic acid detection method including the step of hybridizing a first oligonucleotide probe immobilized on a solid phase with one of single-stranded regions which contain natural nucleotides and are respectively located at opposite ends of an amplified double-stranded DNA fragment.

The amplified double-stranded DNA fragment is obtained by a nucleic acid amplification reaction of a sample DNA as a template using a certain primer set.

The sample DNA is not particularly limited and may be any one usable as a template in the nucleic acid amplification reaction. Specific examples include any DNAs derived from biological samples such as blood, biological fluids, tissues, oral mucosa, hairs, nails, cultured cells, animals, plants, and microorganisms. The sample DNA may be genomic DNA, cDNA, mitochondrial DNA, chloroplast DNA, or the like. Moreover, a cDNA synthesized from a RNA template by reverse transcription may be also used. A suitable one can be appropriately selected from these DNAs according to the DNA fragment to be amplified.

The sample DNA needs not be purified DNA, and cells or a tissue containing the sample DNA can be used directly, without being purified, in the nucleic acid amplification reaction.

The amplified double-stranded DNA fragment having a single-stranded region at each end is preferably a product obtained by a nucleic acid amplification technique using two primers each containing a tag region that is not made double-stranded by a nucleic acid amplification reaction. In this case, the single-stranded regions at both ends of the amplified double-stranded DNA fragment are derived from the tag regions which are not made double-stranded by a nucleic acid amplification reaction, in the primers used in the nucleic acid amplification reaction.

Figure 1:
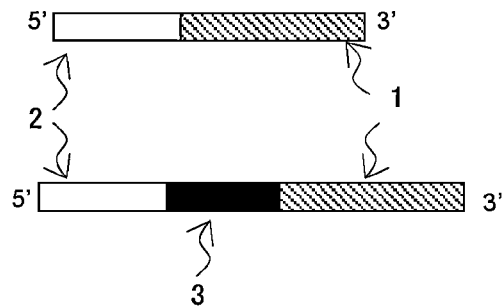
FIG. 1 is a schematic diagram of a PCR primer in the present invention.

FIG. 1 shows a primer for nucleic acid amplification. The primer contains a primer main region 1, and a tag region 2 which is located on the 5' side of the primer main region and which is not made double-stranded by a nucleic acid amplification reaction. The primer may further contain a spacer structure containing a polymerase reaction inhibitory region 3 between the primer main region and the tag region.

Figure 2:
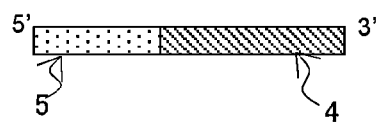
FIG. 2 is a schematic diagram of a first PCR primer in the present invention.
Figure 3:
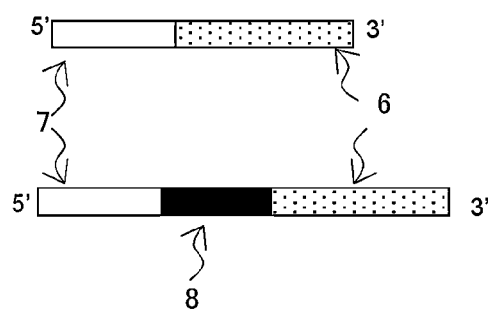
FIG. 3 is a schematic diagram of a second PCR primer in the present invention.

The amplified double-stranded DNA fragment is preferably a product obtained by a nucleic acid amplification technique using a first primer set including primers each containing a sequence capable of hybridizing to a template of the target nucleic acid and a common sequence incapable of hybridizing to the template, and a second primer set including primers each containing a sequence capable of hybridizing to a complementary sequence to the corresponding common sequence and a tag region that is not made double-stranded by a nucleic acid amplification reaction. FIG. 2 shows each primer of a first PCR primer set. This first PCR primer (joint primer) characteristically contains a primer main region 4 capable of hybridizing to a template of the target nucleic acid and a common region 5 located on the 5' side of the primer main region and having a sequence common to a second primer. FIG. 3 shows each primer of a second PCR primer set. This second primer characteristically contains a primer main region 6 having a sequence common to the first primer, and a tag region 7 which is located on the 5' side of the main region 6 and which is not made double-stranded by a nucleic acid amplification reaction. The second primer may contain a spacer structure containing a polymerase reaction inhibitory region 8 between the second primer main region and the tag region.

The term "primer main region" refers to an oligonucleotide region having a base sequence capable of functioning as a primer in the nucleic acid amplification reaction. Specifically, it is a base sequence that is capable of hybridizing to the 5' end or 3' end of a target base sequence of a target nucleic acid, and in general, is a base sequence complementary to a base sequence at the 5' end or 3' end of the target base sequence. The primer main regions may contain base deletions, insertions, and mismatch sites as long as they are capable of specifically binding to the target nucleic acids. The primer main regions preferably have a length of at least 8 bases, more preferably at least 12 bases, and still more preferably at least 15 bases. The maximum chain length of the primers is not particularly limited, and is generally 50 bases or less, preferably 40 bases or less, from the viewpoint of their synthesis costs and other factors.

The tag regions of the primers are not particularly limited, provided that they contain natural nucleotides. The term "natural nucleotide" means a nucleotide composed of a natural base (adenine, thymine, guanine, cytosine, or uracil), a sugar moiety (deoxyribose or ribose), and phosphate group (s), all of which are not artificially modified. The natural nucleotides may be D-nucleotides or L-nucleotides. The term "D-nucleotide" refers to a nucleotide containing D-deoxyribose or D-ribose. Likewise, the term "L-nucleotide" refers to a nucleotide containing L-deoxyribose or L-ribose. The effect of such tag regions containing natural nucleotides is to allow easy synthesis at low cost. The proportion of natural nucleotides in the tag region of the primer is preferably at least 5%, more preferably at least 20%, still more preferably at least 50%, further more preferably at least 70%, and most preferably at least 90%. The length of the tag region is not particularly limited, and the tag region has only to be long enough to hybridize to a complementary nucleic acid strand. The length is generally 5 bases to 60 bases, preferably 6 bases to 40 bases.

The tag regions of the primers each preferably have a nucleic acid sequence in the same orientation as the primer main region. The effect of the tag regions of the primers each having a nucleic acid sequence in the same orientation as the primer main region is to allow easy synthesis at low cost. Even if the tag region and the primer main region are not directly linked to each other (e.g., a non-natural compound such as azobenzene is inserted between the tag region and the primer main region), these regions preferably have sequences in the same orientation as each other. The nucleic acids being in the same orientation means that adjacent nucleotides are linked to each other via a 5'-3', not a 3'-3' or 5'-5', phosphodiester bond between the sugar moieties of the nucleotides. For example, in the case of a tag region where nucleotides are linked to one another via a 5'-3' phosphodiester bond between the sugar moieties, the nucleotides in the main region are also linked to one another via a 5'-3' bond between the sugar moieties.

The polymerase reaction inhibitory region is not particularly limited, provided that it inhibits a nucleic acid extension reaction catalyzed by a polymerase to maintain the single-stranded structure in the region. Examples of such a structure include nucleic acid sequences having a three-dimensional structure that inhibits the progress of DNA polymerase, such as a tight hairpin structure and a pseudoknot structure; non-natural nucleic acids such as L-nucleic acids and artificial nucleic acids, RNA, and non-nucleic acid structures such as aliphatic chains.

The terms "hairpin structure" and "pseudoknot structure" refer to stable loop structures formed by pairing with another single-stranded region in the same molecule. L-DNA, which is DNA containing L-deoxyribose, does not function as a template in DNA extension reactions because it is not recognized by generally used DNA polymerases. In addition, L-DNA forms a left-handed double helix, and thus is incapable of hybridizing to naturally-occurring D-nucleic acids and capable of hybridizing only to nucleic acids of the same L-form. The term "artificial nucleic acids" refers to nucleic acids into which a compound that is not present in natural nucleic acid sequences is artificially inserted. Examples include, but are not limited to, peptide nucleic acids (PNA), bridged nucleic acids (BNA and LNA), azobenzene, fluorescein, Cy3, and Cy5.

PNA refers to a molecule having a structure similar to DNA and RNA but having a backbone including a peptide structure. The backbone includes N-(2-aminoethyl)-glycine units linked by amide bonds. Further, purine and pyrimidine rings, which correspond to nucleic-acid bases, are linked to the backbone through a methylene group and a carbonyl group. BNA (LNA) refers to nucleic acids artificially synthesized by modifying the sugar moiety of DNA or RNA to form a bridge.

In the case that the tag region consists only of natural nucleotides and has a nucleic acid sequence in the same orientation as the primer main region, the polymerase reaction inhibitory region is typically necessary between the tag region and the primer region. On the other hand, in the case that the tag region is incapable of functioning as a template in the reaction catalyzed by a DNA polymerase and thus is not made double-stranded by the nucleic acid amplification reaction, just like L-nucleic acids, artificial nucleic acids and the like, the polymerase reaction inhibitory region can be omitted. Moreover, the primer in the present invention may contain only one of structures such as stable loop structures (e.g. hairpin structures, pseudoknot structures), non-natural nucleic acids (e.g. L-nucleic acids, artificial nucleic acids), and non-nucleic acid structures (e.g. aliphatic chains), or may contain two or more of these structures in combination.

The primer can be labeled with various molecules generally used for oligonucleotide labeling. Examples of such molecules include enzymes, magnetic particles, fluorescent pigments, and radioisotopes. Any of these may be used alone, or two or more of these may be used in combination.

The primers thus designed can be produced by any methods without particular limitation, and known methods can be used. Specifically, the designed primers can be easily obtained with a DNA synthesizer or from a custom synthesis service.

The nucleic acid amplification technique is not particularly limited, provided that it produces an amplified double-stranded DNA fragment having at each end thereof a single-stranded region containing natural nucleotides, using the primers mentioned above. One example thereof is PCR. Isothermal amplification techniques such as LAMP and ICAN may also be used.

In the case where the nucleic acid amplification technique is PCR, a pair of reverse and forward primers for the PCR reaction may be designed such that both primers contain different polymerase reaction inhibitory regions from each other, or such that one of them contains a polymerase reaction inhibitory region and the other is free of any polymerase reaction inhibitory region but is modified with biotin or the like.

The PCR conditions are not particularly limited, provided that a target region of the above-described sample DNA is amplified by PCR using the sample DNA as a template and the primer set. Specifically, the polymerase used in the PCR is not particularly limited, and is preferably a heat-stable DNA polymerase, and more preferably a heat-stable polymerase that does not substantially have a 3'-to-5' exonuclease activity. One non-limiting example of such heat-stable DNA polymerases is Ex-Taq (available from TAKARA BIO INC.). Likewise, the PCR reaction conditions including temperature, time, and buffer composition are not particularly limited, and may appropriately be determined according to the DNA polymerase selected to use, the sequences of the primers, the length of the target sequence, and other factors. The length of the DNA to be amplified by the nucleic acid amplification reaction is preferably at least 20 bases, and more preferably at least 40 bases. If the length is less than 20 bases, the probability of non-specific amplification tends to be increased.

Figure 4:
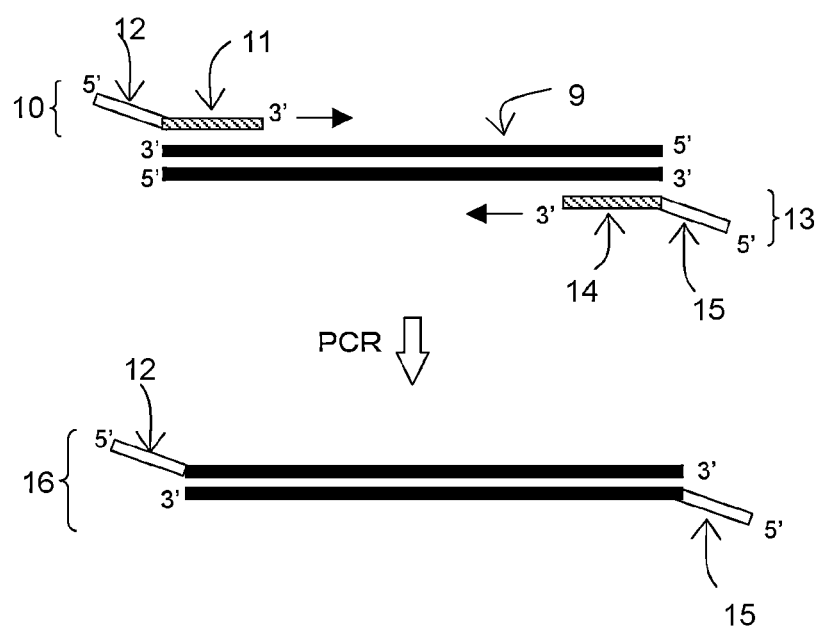
FIG. 4 is a schematic flow diagram of synthesis of a partially double-stranded nucleic acid in the present invention.

PCR can be carried out in a conventional manner using the primer set to provide an amplification product in which a single-stranded region is added to each end of the target nucleic acid sequence. FIG. 4 is a schematic flow diagram of an exemplary amplification reaction using primers each containing a primer main region and a tag region. The forward primer 10 contains a primer main region 11 having the same sequence as apart of the 5' end of a target nucleic acid sequence 9, and a tag region 12 located on the 5' end of the primer main region 11. The reverse primer 13 contains a primer main region 14 having a complementary sequence to a part of the 3' end of the target nucleic acid sequence, and a tag region 15 located on the 5' end of the primer main region 14. The linked tag region in each primer typically has a different sequence from each other. The primer set is used in PCR to afford an amplified DNA product 16 having a single-stranded region at each end because the added tag regions of both primers are not substantially involved in the PCR reaction. The amplified DNA fragment having a single-stranded region at each end refers to an amplified DNA product having a double-stranded DNA part that is the same as the target DNA region, and also having single-stranded regions which are respectively located as 5' end tag parts at opposite ends of the double-stranded DNA part, as shown in FIG. 4. The amplified DNA fragment more specifically refers to an amplified double-stranded DNA fragment having at each end thereof a single-stranded region that includes non-modified nucleic acids, wherein the single-stranded region at each end has a sequence in the same orientation as the corresponding DNA strand which it is located next to.

Figure 5:
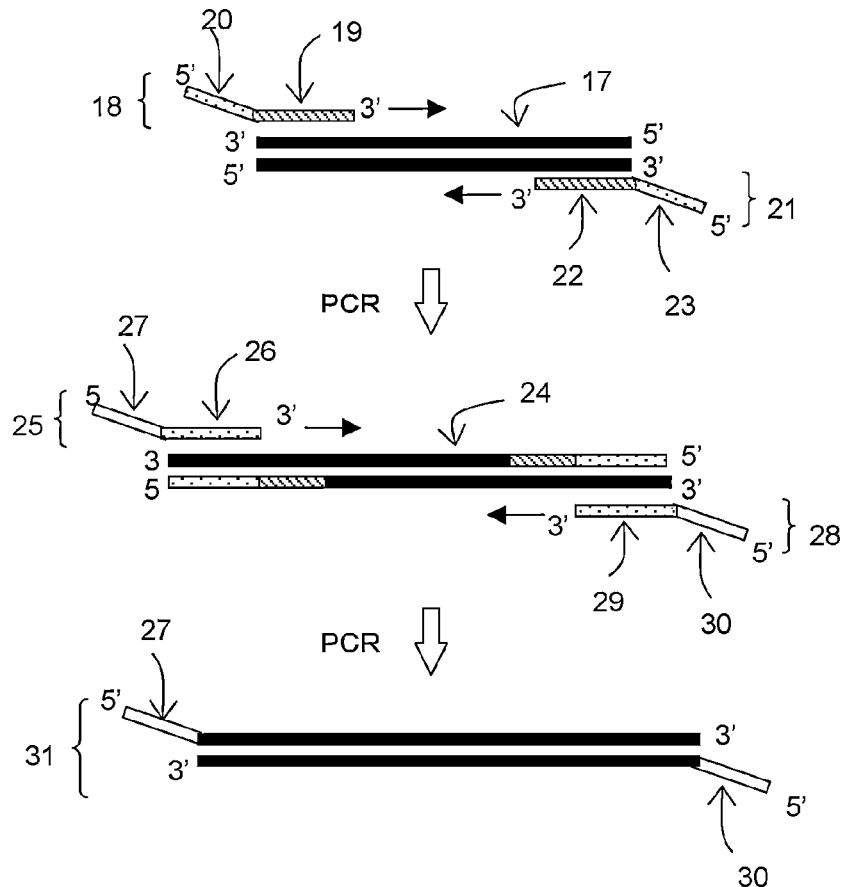
FIG. 5 is a schematic flow diagram of synthesis of a partially double-stranded nucleic acid in another embodiment of the present invention.

FIG. 5 is a schematic flow diagram of an exemplary amplification reaction using primers each containing a primer main region and a common sequence region as a joint primer set, and primers each containing the common sequence region and a tag region. PCR can be carried out in a conventional manner using the first and second primer sets to provide an amplification product in which a single-stranded region is added to each end of the target nucleic acid sequence.

The first forward primer 18 contains a primer main region 19 having the same sequence as a part of the 5' end of a target nucleic acid sequence 17, and a common sequence region 20 located on the 5' end of the primer main region 19. The first reverse primer 21 contains a primer main region 22 having a complementary sequence to a part of the 3' end of the target nucleic acid sequence, and a common sequence region 23 located on the 5' end of the primer main region 22. The added common sequence regions of both primers typically have different sequences from each other. The first primer set is used in the PCR reaction to afford an amplified double-stranded DNA product 24 containing the common regions.

Moreover, the second forward primer 25, which is shown around the common sequence region at either end of the amplified DNA product 24, contains a primer main region 26 having a sequence common to a part of the 5' end of the amplified double-stranded DNA product 24 containing the common regions, and a tag region 27 located on the 5' end of the primer main region 26. The second reverse primer 28 contains a primer main region 29 having a complementary sequence common to a part of the 3' end of the amplified double-stranded DNA product 24 containing the common regions, and a tag region 30 located on the 5' end of the primer main region 29. The linked tag regions of both primers typically have different sequences from each other. The primer set is used in PCR to afford an amplified DNA product 31 having a single-stranded region at each end because the added tag regions of both primers are not substantially involved in the PCR reaction. In this embodiment, the PCR reaction using the first primers and then the PCR reaction using the second primers are sequentially carried out as shown in FIG. 5. With respect to the order, the first and second primers may be added at the same time, or alternatively, the second primers may be added later.

The amplified DNA fragment having a single-stranded region at each end refers to an amplified DNA product having a double-stranded DNA part that is the same as the target DNA region, and also having single-stranded regions which are respectively located as 5' end tag parts at opposite ends of the double-stranded DNA part, as denoted by the reference numeral 31 in FIG. 5.

In the case of using such first and second primer sets, a single set of second primers can be used for different target nucleic acids to provide the same single-stranded tag sequences, as long as these primer sets are designed to have the same common sequences. The amplified DNA fragment more specifically refers to an amplified double-stranded DNA fragment having at each end thereof a single-stranded region that includes non-modified nucleic acids, wherein the single-stranded region at each end has a sequence in the same orientation as the corresponding DNA strand which it is located next to.

The single-stranded regions of the amplification product synthesized using the primers are used to form a hybridization complex. The term "hybridization" means that molecules containing nucleic acids complementarily form a complex (e.g. DNA/DNA, DNA/RNA, DNA/PNA, L-DNA/L-DNA). In the nucleic acid detection method of the present invention, the amplified DNA product obtained in the nucleic acid amplification step can be used in a hybridization reaction without the need of a treatment for making the amplified product single-stranded (e.g. heat treatment) and other treatments because the amplified DNA fragment contains the single-stranded regions.

It is possible to hybridize a first oligonucleotide probe immobilized on a capture carrier (solid phase) with one of single-stranded tag regions which contain natural nucleotides and are respectively located at opposite ends of the amplified double-stranded DNA fragment. The detection method preferably further includes the step of hybridizing a second oligonucleotide probe labeled directly or indirectly with a labeling substance with the other single-stranded region of the amplified double-stranded DNA fragment. The formation of a triple complex of the amplified double-stranded DNA fragment, the first oligonucleotide probe, and the second oligonucleotide probe is called "sandwich hybridization". The order of hybridization of the three substances is not particularly limited.

The length of the first oligonucleotide probe is not particularly limited as long as it is capable of hybridizing to the single-stranded region of the amplified double-stranded DNA fragment, and is preferably 5 to 60 bases, and more preferably 10 to 40 bases.

The length of the second oligonucleotide probe is not particularly limited as long as it is capable of hybridizing to the single-stranded region of the amplified double-stranded DNA fragment, and is preferably 5 to 60 bases, and more preferably 10 to 40 bases.

The labeling substance bound to the second oligonucleotide probe is not particularly limited as long as it enables the amplified double-stranded DNA fragment to be detected. The labeling substance is preferably a colored carrier that enables the amplified double-stranded DNA fragment to be visually detected. Examples of such colored carriers include colored particles, and enzyme- or pigment-bound carriers. Preferred among these are colored particles.

Examples of the colored particles include colloidal particles of metals such as gold, silver, copper and platinum, colored latexes which are latexes colored with a pigment, a dye or the like, and silica nanoparticles which are silica (silicon dioxide) particles in which pigment molecules are immobilized. Preferred among these are colloidal gold particles and colored (e.g. blue, red) latex particles made of a water-dispersible polymer. The use of such colored particles allows the amplified DNA fragment to be visually determined more easily. In particular, in the case of simultaneously detecting multiple analytes, colored particles of different color is used for each analyte to allow the multiple analytes to be visually determined easily at the same time.

In the case where colored particles are used, the particles size is not particularly limited. Preferably, the particle size is determined such that the colored particles have less adverse effect on the formation of a sandwich hybridization complex and on the capturing of the target sequence-containing amplification product on the solid phase, and provide good color development in the detection. The particle size of colored particles is selected to be smaller than the pore size of a later-described chromatographic medium. Specifically, the particle size is typically not more than 500 nm, preferably 0.1 nm to 100 nm, and more preferably 1 nm to 50 nm. The enzymes usable as the colored carrier are proteins that catalyze reactions of substrates to develop a color or emit light. Examples include peroxidases, alkaline phosphatases, and luciferases, although the enzymes are not limited to these examples, provided that they allow detection by observation with the naked eye.

The conditions of the hybridization of the single-stranded region at the end of the amplified double-stranded DNA fragment and the first or second oligonucleotide probe are not particularly limited, provided that they can hybridize to each other. Preferably, they are reacted at room temperature in 10 mM phosphate buffer. In this case, the hybridization rate can be increased by adding a salt such as sodium chloride.

The presence of the target nucleic acid can be assessed by detecting the target substance in the sandwich hybridization complex formed in an identifiable zone on the capture carrier (solid phase). The detection is preferably based on visual observation. According to the detection method of the present invention, the amplification product of the nucleic acid amplification reaction can be used directly in the hybridization reaction without the need of any treatment for making the amplification product single-stranded (e.g. heat denaturation). In addition, it is possible to easily and rapidly assess the presence of the target nucleic acid by visual observation without the need of special equipment.

The nucleic acid detection method involving the formation of a sandwich hybridization complex is preferably carried out on a nucleic acid detection device. In addition, it is preferable to use chromatography for the detection of the amplified DNA product.

Figure 6:
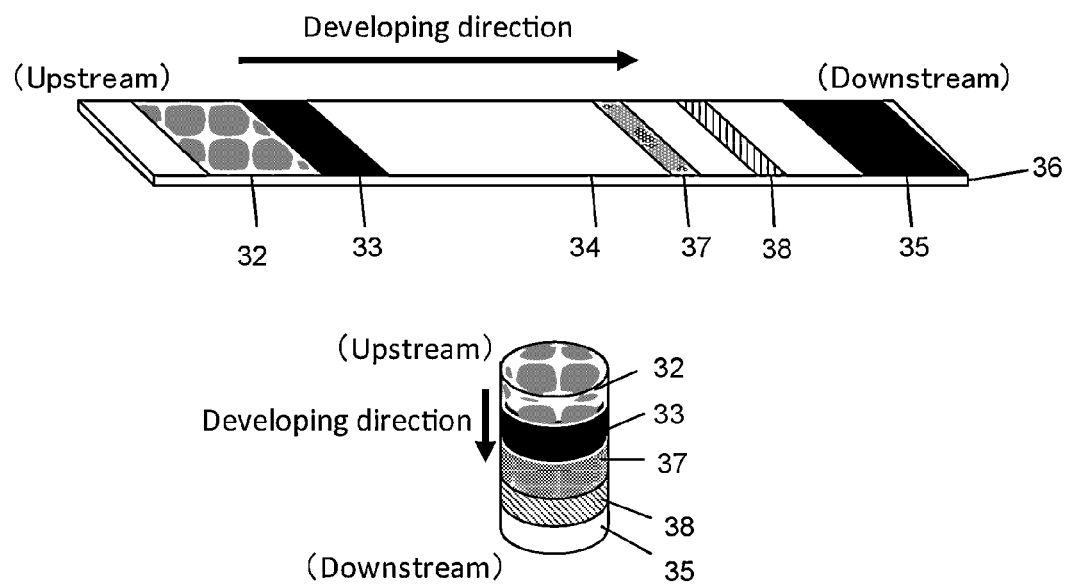
FIG. 6 is a schematic diagram of an exemplary nucleic acid chromatography device of the present invention.

The nucleic acid chromatography device of FIG. 6 includes a sample pad 32 (a carrier to which the amplified DNA product is to be applied), a conjugate pad 33 (a carrier in which a colored carrier-bound oligonucleotide is placed), a carrier 34 having a capture oligonucleotide (a chromatographic medium), and an absorption pad 35, and these members are attached on a supporting member 36 with a pressure-sensitive adhesive or the like. The carrier 34 is provided with a test line 37 along which the capture oligonucleotide is applied, and a control line 38. In the case where the colored carrier-bound oligonucleotide is mixed with a developing solution, the conjugate pad 33 may not be used.

Preferably, the chromatography is carried out to detect the amplified double-stranded DNA fragment by a method including the following steps (a) to (c): (a) placing the amplified DNA fragment in a zone on the nucleic acid detection device which is different from a zone where the first oligonucleotide probe is immobilized; (b) diffusing the amplified DNA fragment with a solvent on the device toward the zone where the first oligonucleotide probe is immobilized; and (c) hybridizing the first oligonucleotide probe with the amplified DNA fragment in the zone where the first oligonucleotide probe is immobilized.

For example, in the nucleic acid chromatography device of FIG. 6, the amplified DNA fragment is placed on the sample pad 32 in the step (a). In the step (b), the amplified DNA fragment is diffused in the direction of the arrow. In the step (c), the amplified DNA fragment is hybridized with and captured by the first oligonucleotide probe immobilized on the test line 37.

Preferably, the detection method further includes the step of hybridizing the second oligonucleotide probe labeled with the labeling substance with the amplified DNA fragment before the step (c). For example, in the case of the nucleic acid chromatography device of FIG. 6, the amplified DNA fragment and the second oligonucleotide probe are hybridized on the conjugate pad 33.

Moreover, the chromatography is preferably carried out by the following steps (d) to (h): (d) placing the amplified DNA fragment and the second oligonucleotide probe labeled with the labeling substance respectively in discrete zones on the nucleic acid detection device which are different from a zone where the first oligonucleotide probe is immobilized; (e) diffusing the amplified DNA fragment with a solvent toward the zone where the second oligonucleotide probe labeled with the labeling substance is placed; (f) hybridizing the second oligonucleotide probe labeled with the labeling substance with the amplified DNA fragment in the zone where the second oligonucleotide probe labeled with the labeling substance is placed; (g) diffusing a hybridization complex obtained in the step (f) on a development medium toward the zone where the first oligonucleotide probe is placed; and (h) hybridizing the first oligonucleotide probe with the complex in the zone where the first oligonucleotide probe is immobilized.

For example, in the case of the nucleic acid chromatography device of FIG. 6, the amplified DNA fragment is placed on the sample pad 32, and the second oligonucleotide probe is placed on the conjugate pad 33 in the step (d). In the step (e), the amplified DNA fragment is diffused from the sample pad 32 in the direction of the arrow. In the step (f), the amplified DNA fragment and the second oligonucleotide probe are hybridized on the conjugate pad 33. In the step (g), the hybridization complex of the amplified DNA fragment and the second oligonucleotide probe labeled with the labeling substance is diffused in the direction of the arrow. In the step (h), the first oligonucleotide probe and the complex are hybridized on the test line 37.

On the test line on the membrane, an oligonucleotide probe having a complementary sequence to one of the tag regions of the amplified DNA fragment is immobilized as the first oligonucleotide probe for capturing. The first oligonucleotide probe for capturing may be bound to the membrane directly or via a functional group or a certain substance. Examples of such mediating substances include, but are not limited to, peptides, proteins and nucleic acids. In the case where avidin is used as a mediating substance, the capture oligonucleotide should be modified with biotin.

On the control line on the membrane, an oligonucleotide probe for capturing the colored carrier is immobilized. The oligonucleotide probe for the control line has a complementary sequence to the second oligonucleotide probe labeled with the labeling substance so that it certainly captures the labeling substance when the sample solution is developed. The oligonucleotide probe for the control line may also be bound to the membrane directly or via a functional group or a substance, as described above. Examples of mediating substances include, but are not limited to, peptides, proteins and nucleic acids. In the case where avidin is used as a mediating substance, the capture oligonucleotide should be modified with biotin.

The presence of the target nucleic acid in a sample can be assessed by visually observing a color on the test line. Also, a color on the control line can be visually observed to determine whether the development and the color reaction are normally carried out. The "to visually observe" means observation with the naked eye to assess the color.

Examples of the chromatographic medium include paper filters such as qualitative filters, quantitative filters, phase separating filters, glass fiber filters, silica fiber filters, and bicomponent fiber filters. Other examples include filters made of celluloses (e.g. nitrocellulose), synthetic resin films such as polyethersulfone membranes, and porous gels such as silica gel, agarose, dextran, and gelatin. Nylon membranes can also be suitably used. In practical use, the form and size of the chromatographic medium are not particularly limited, and may be any suitable ones in operation and observation of the reaction results.

These carriers may be modified in various ways to improve the hydrophilicity and affinity for the compound. In order to make the operation easier, the back surface of the chromatographic medium whose opposite surface is provided with reaction sites is preferably provided with a supporting material made of plastic or the like.

The developing direction in the device is not particularly limited, and may be horizontal or vertical as shown in FIG. 6. Since the solvent used in the nucleic acid amplification reaction can function as a developing solvent as well, the reaction solution obtained by the nucleic acid amplification reaction can be directly dropped to the sample pad 32 in FIG. 6. Alternatively, a separate developing solution may be added to the reaction solution obtained by the amplification reaction, and the resulting solution may be added to the sample pad. Any developing solvent can be used without particular limitation, provided that it is liquid. Examples thereof include phosphate buffer and Good's buffers such as Tris buffer. Such solvents may contain salts, surfactants, proteins, and nucleic acids dissolved therein.

Figure 7:
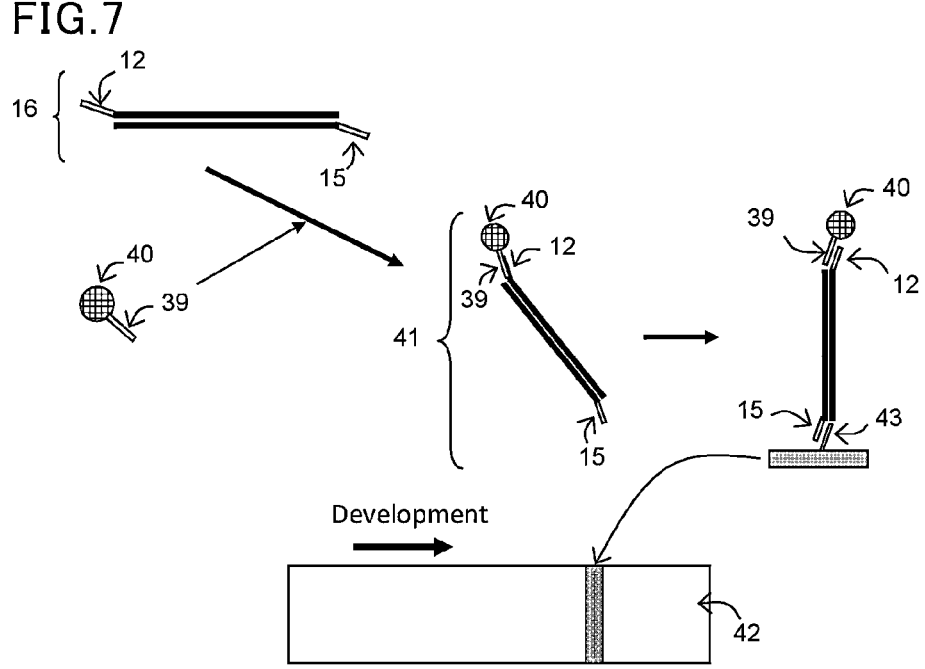
FIG. 7 is a schematic flow diagram of the principle of PCR product detection in the present invention.

With reference to FIG. 7, an exemplary embodiment of the present invention is described in which a sandwich hybridization complex is formed on a chromatographic carrier. An amplified DNA fragment 16 obtained in the nucleic acid amplification step is used in the subsequent complex formation step without performing a treatment for making the fragment single-stranded (e.g. heat treatment) and other treatments. Then, the amplified DNA fragment 16 is hybridized with an oligonucleotide probe including a colored carrier 40 and a nucleic acid sequence 39 capable of specifically binding to one (tag region 12) of the tag regions of the DNA fragment, and thereby forms a first complex 41. The complex 41 may be formed, for example, in a PCR reaction vessel, prior to the application to the development medium, or may be formed by applying the amplified DNA fragment to the carrier and allowing the amplified DNA fragment to move by capillary action to pass through a carrier that has been subjected to coating with the labeling molecule-bound oligonucleotide and drying.

The complex 41 comes into contact with a capture oligonucleotide probe 43 that is previously allowed to be bound in an identifiable zone on a chromatographic medium 42 made of a porous membrane or the like, on the development medium. The capture oligonucleotide 43 has a complementary sequence to the other tag sequence 15 of the amplified DNA fragment, and thus hybridizes to the complex 41 to form a sandwich hybridization complex.

The order of procedures for forming such a sandwich hybridization complex is not particularly limited. It is preferable that the amplified DNA fragment and the second oligonucleotide probe labeled with the labeling substance form a complex 41, and then the complex and the first oligonucleotide probe for capturing form a complex. Alternatively, a sandwich hybridization complex may be formed by enriching the amplified DNA fragment via the first oligonucleotide probe for capturing on the development medium, and then developing the second oligonucleotide labeled with the labeling substance.

Figure 8:
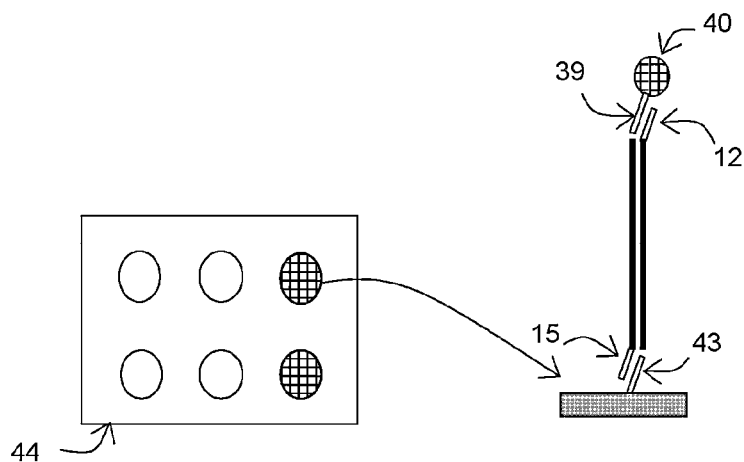
FIG. 8 is a schematic diagram of an exemplary microarray (DNA chip) of the present invention.

Another example of the nucleic acid detection device is a microarray (DNA chip) as shown in FIG. 8. The triple complex can be formed by sandwich hybridization in wells of the microarray 44 in which a capture oligonucleotide is immobilized.

Figure 9:
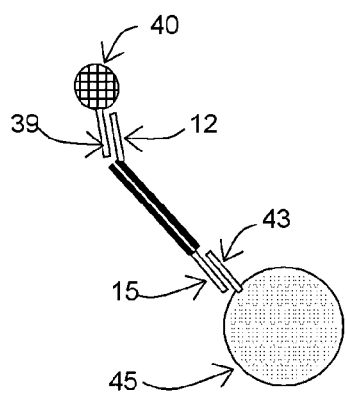
FIG. 9 is a schematic diagram of an exemplary bead carrier in the present invention.

Still another example is a bead form as shown in FIG. 9. The triple complex can be formed by sandwich hybridization on the bead carrier 45 having a capture oligonucleotide.

The nucleic acid detection method and the nucleic acid detection device of the present invention can be used for any techniques involving a nucleic acid amplification step. In other words, the nucleic acid detection method and the nucleic acid detection device of the present invention can be used for techniques in any fields which involve detection of an amplified DNA fragment (e.g. PCR product) obtained by a nucleic acid amplification technique. Specifically, they are used for, for example, molecular biology research, detection of pathogens, detection of foreign matter such as allergens in foods, food quality control (inspection of mislabeled foods and genetically modified foods), livestock control, detection of single nucleotide polymorphisms (hereinafter, also referred to as "SNP"), screening of diseases such as cancer, and so on. Accordingly, the present invention encompasses methods for detecting a pathogenic infectious disease, methods for detecting foreign matter (e.g. allergen) in foods, food quality control methods, livestock control methods, methods for detecting a single nucleotide polymorphism, and like methods which include a step of performing the nucleic acid detection method of the present invention.

As embodiments of application of the present invention, a pathogen detection method and an allergen detection method according to the present invention are described in detail below.

The pathogen detection method according to the present invention may be any method including the step of detecting a gene specific to a pathogen by the nucleic acid detection method of the present invention. The pathogen is not particularly limited, and specific examples include pathogenic bacteria, pathogenic viruses, food poisoning bacteria, and bacteria and viruses causing hospital infections. More specifically, there may be mentioned, for example, viruses such as hepatitis C virus (HCV), cytomegalovirus (CMV), Epstein-Barr virus (EBV), herpesviruses, and human immunodeficiency virus (HIV); bacteria such as *Escherichia coli* (e.g. O157), *Mycobacterium tuberculosis, Salmonella typhi, salmonella* bacteria, and *Vibrio parahaemolyticus*; and microorganisms such as mycoplasma.

More specifically, the pathogen detection method according to the present invention includes determining, by the nucleic acid detection method, whether a gene specific to a pathogen is present, for example, in a DNA sample prepared from a sample to be assessed for the presence of the pathogen. Or, a sample to be assessed for the presence of the pathogen may be directly used for a template for nucleic acid amplification without preparing a DNA sample. For example, in the case where the pathogen to be detected is a bacterium such as *Escherichia coli*, a bacterial colony suspension can be used for a template. Then, if the gene specific to the pathogen is detected, it can be determined that the sample contains the pathogen. In this manner, it is possible to easily and highly accurately determine whether a sample contains a pathogen without the need of special equipment. Thus, the pathogen detection method according to the present invention can be used for the diagnosis of microbial infectious diseases.

The allergen detection method according to the present invention may be any method including the step of detecting a gene encoding an allergen by the nucleic acid detection method of the present invention. The allergen is not particularly limited, and specific examples include allergens contained in foods. More specifically, there may be mentioned, for example, egg albumen allergens, milk allergens, wheat allergens, buckwheat allergens, peanut allergens, and so on. More specifically, the allergen detection method according to the present invention includes determining, by the nucleic acid detection method, whether a gene encoding an allergen derived from egg, milk, wheat, buckwheat, peanut or the like is present, for example, in a DNA sample prepared from a food. Then, if such a gene is detected, it can be determined that the food contains an ingredient containing the allergen.

In this manner, it is possible to easily and highly accurately determine whether a sample such as food contains an ingredient containing an allergen without the need of special equipment. It should be noted that the allergen origin is not limited to those described above. For example, taking the example of grains, the allergen origin may be any type of rice, corn, Italian millet, proso millet, Japanese millet, buckwheat, or pulses. Since DNA is thermally stable, a trace amount of DNA can be detected even in processed foods. Thus, the allergen detection method according to the present invention provides data that can be used not only for food labeling and allergen information of foods but also for detection of minute amounts of residual food additives (e.g. processing materials, carry-overs) and detection of contaminants that are not intended by a manufacturer (e.g. the presence or absence of cross-contamination between the manufacturing lines).

In addition to these applications, the present invention is applicable to determination of the parentage of a mammal including human, identification of the pedigree of livestock, variety identification for agricultural products, SNP detection, detection of diseases (e.g. cancer) caused by gene mutations, and the like. More specifically, for example, taking the example of livestock, the present invention can be used for pedigree registration, individual identification, parentage determination, removal of a carrier individual with a disease-causing gene, and the like. It should be noted that the present invention is not limited to the embodiments mentioned above, but may be modified within the scope of the appended claims. An embodiment based on a proper combination of technical means disclosed in different embodiments is encompassed in the technical scope of the present invention.

EXAMPLES

The present invention is described in more detail below, referring to examples which are not to be construed as limiting the technical scope of the present invention.

Example 1

(1) Synthesis of L-DNA-Tagged Primers

In this example, a forward primer (F) and a reverse primer (R) were designed to be able to amplify about 330 base pairs by PCR amplification using pUC19 (available from Takara Bio, Inc.) as a template. Then, tag sequences T1 and T2 which are non-natural (L-) DNA strands were respectively introduced into the 5' ends of these primers to construct L-DNA-tagged primers T1-F and T2-R. The synthesis of these L-DNA-tagged primers was carried out by a general phosphoramidite method using a DNA automatic synthesizer (H-8-SE: Gene World) with a 0.2 μM column.

The following shows the primer set prepared in this study.

Primer F:
(SEQ ID No: 1)
5'-$^D$d(GGAAACAGCTATGACCATGA)-3'

Primer R:
(SEQ ID No: 2)
5'-$^D$d(CTATGCGGCATCAGAGCAG)-3'

Tag sequence T1:
(SEQ ID No: 3)
5'-$^L$d(GACAACGGAGACAGAGCCAA)-3'

Tag sequence T2:
(SEQ ID No: 4)
5'-$^L$d(ATGCTACCGTATGCCCAGTG)-3'

Primer T1-F:
(SEQ ID No: 5)
5'-$^L$d(GACAACGGAGACAGAGCCAA)-$^D$d(GGAAACAGCTATGACCATGA)-3'

Primer T2-R:
(SEQ ID No: 6)
5'-$^L$d(ATGCTACCGTATGCCCAGTG)-$^D$d(CTATGCGGCATCAGAGCAG)-3'

(2) PCR Using L-DNA-Tagged Primer Set

PCR was performed using the primer set prepared by performing the above step (1). Specifically, a 100 μl PCR mixture was prepared by putting the prepared primer F and primer R (15 pmol each) and pUC19 (10 ng) in a 0.2-ml PCR tube, and following the instruction manual of a PCR device ExTaq (available from Takara Bio, Inc.). Thereafter, the tube was set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. Consequently, the target fragment of about 330 bp was amplified. Separately, the same reaction was carried out in the absence of pUC19 as a negative control.

(3) Preparation of Latex-Bound L-Oligonucleotide Probe

A carboxyl group-containing polystyrene latex (solids content: 10% (w/w), available from Bangs Laboratories, Inc.) and an amino-group containing L-oligonucleotide probe (SEQ ID No: 7, strand complementary to SEQ ID No: 3) were bonded by mixing them in MES buffer containing a necessary amount of a water-soluble carbodiimide, and the resulting product was blocked with monoethanolamine. The reaction solution was centrifuged, and the supernatant was then removed. The obtained precipitate was washed with water, and then resuspended in HEPES buffer with a surfactant. The suspension was uniformly applied to a glass fiber pad, and the pad was dried in a vacuum oven. In this manner, a conjugate pad was obtained.

Nucleotide probe 1:
(SEQ ID No: 7)
5'-$^L$d(TTGGCTCTGTCTCCGTTGTC)-NH$_2$-3'

(4) Immobilization of L-Oligonucleotide Probe on Solid Phase

A nylon membrane modified with carboxyl groups (available from Pall Corporation, 6 mm×60 mm) was treated with a water-soluble carbodiimide, and washed with deionized water. An amino group-containing L-oligonucleotide probe having a sequence (SEQ ID No: 8) complementary to SEQ ID No: 4 was applied to the activated membrane with a dispenser along a line drawn 30 mm from one end of the membrane, and air-dried for 15 minutes. Subsequently, the membrane was treated with Tris buffer and blocked, and then washed with water and dried.

```
Nucleotide probe 2:
                                        (SEQ ID No: 8)
5'-Ld(CACTGGGCATACGGTAGCAT)-NH2-3'
```

(5) Preparation of Nucleic Acid Chromatography-Like Test Strip

A test strip to be used for detection of the PCR product amplified using the L-DNA-tagged primer set was prepared by attaching a chromatographic medium consisting of the nylon membrane prepared above, the conjugate pad prepared above, a general sample pad as a sample application zone, and an absorption pad for absorbing the developed sample and the labeling substance to a substrate consisting of a backing sheet as shown in FIG. 6.

(6) Detection of PCR Product Using Test Strip

The PCR product obtained in the step (2) was immediately, without being denatured, applied to the sample application zone on the test strip prepared in the step (5) to perform detection by chromatography. A colored line specific to the target nucleic acid was detected along the test line for the sample prepared using pUC19 as an analyte in the step (2). In contrast, there was no line detected for the negative control prepared using water instead. The detection by chromatography took as short a time as 10 to 15 minutes.

Example 2

(1) Synthesis of Hairpin-Tagged Primers

In the same manner as in the step (1) in Example 1, a forward primer (F) and a reverse primer (R) were designed to be able to amplify about 330 base pairs by PCR amplification using pUC19 (available from Takara Bio, Inc.) as a template. Then, a polymerase reaction inhibitory region (H) having a hairpin structure and a tag sequence T3 or T4 were introduced into the 5' end of each corresponding primer to synthesize tagged primers T3-H—F and T4-H—R.

The following shows the primer set prepared in this study.

```
Polymerase reaction inhibitory sequence H:
                                        (SEQ ID No: 9)
5'-Dd(AGGCGAGGTCGCGAGCGCACATGTGCG
CTCGCGACCTC GCCT)-3'

Tag sequence T3:
                                        (SEQ ID No: 10)
5'-Dd(TATGATATGCTTCTCCACGCATAAT)-3'

Tag sequence T4:
                                        (SEQ ID No: 11)
5'-Dd(TGCTCTGTACACTTGCTCAAT)-3'

Primer T3-H-F:
                                        (SEQ ID No: 12)
5'-Dd(TATGATATGCTTCTCCACGCATAATAGGCGAGGTC
GCGAGCGCACATGTGCGCTCGCGACCTCGCCTGGAAACA
GCTATGACCATGA)-3'

Primer T4-H-R:
                                        (SEQ ID No: 13)
5'-Dd(TGCTCTGTACACTTGCTCAATAGGCGAGGTCGCGA
GCGCACATGTGCGCTCGCGACCTCGCCTCTATGCGGCA
TCAGAGCAG)-3'
```

(2) PCR Using Hairpin-Tagged Primer Set

PCR was performed using the primer set prepared by performing the above step (1). Specifically, a 100 μl PCR mixture was prepared by putting the prepared primer F and primer R (15 pmol each), and pUC19 (10 ng) in a 0.2-ml PCR tube, and following the instruction manual of a PCR device ExTaq (available from Takara Bio, Inc.). Thereafter, the tube was set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. Consequently, the target fragment of about 330 bp was amplified. Separately, the same reaction was carried out in the absence of pUC19 as a negative control.

(3) Preparation of Latex-Bound Oligonucleotide Probe

A carboxyl group-containing polystyrene latex (solids content: 10% (w/w), available from Bangs Laboratories, Inc.) and an amino-group containing oligonucleotide probe (SEQ ID No: 14, strand complementary to SEQ ID No: 10) were bonded by mixing them in MES buffer containing a necessary amount of a water-soluble carbodiimide, and the resulting product was blocked with monoethanolamine. The reaction solution was centrifuged, and the supernatant was then removed. The obtained precipitate was washed with water, and then resuspended in HEPES buffer with a surfactant. The suspension was uniformly applied to a glass fiber pad, and the pad was dried in a vacuum oven. In this manner, a conjugate pad was obtained.

```
Oligonucleotide probe 3:
                                        (SEQ ID No: 14)
5'-Dd(ATTATGCGTGGAGAAGCATATCATA)-NH2-3'
```

(4) Immobilization of Oligonucleotide Probe on Solid Phase

A nylon membrane modified with carboxyl groups (available from Pall Corporation, 6 mm×60 mm) was treated with a water-soluble carbodiimide, and washed with deionized water. An amino group-containing L-oligonucleotide probe having a sequence (SEQ ID No: 15) complementary to SEQ ID No: 11 was applied to the activated membrane with a dispenser along a line drawn 30 mm from one end of the membrane, and air-dried for 15 minutes. Subsequently, the membrane was treated with Tris buffer and blocked, and then washed with water and dried.

```
Oligonucleotide probe 4:
                                        (SEQ ID No: 15)
5'-Dd(ATTGAGCAAGTGTACAGAGCA)-NH2-3'
```

(5) Preparation of Nucleic Acid Chromatography-Like Test Strip

A test strip to be used for detection of the PCR product amplified using the hairpin-tagged primer set was prepared by attaching a chromatographic medium consisting of the nylon membrane prepared above, the conjugate pad prepared above, a general sample pad as a sample application zone, and an absorption pad for absorbing the developed sample and the labeling substance to a substrate consisting of a backing sheet as shown in FIG. 6.

(6) Detection of PCR Product Using Test Strip

The PCR product obtained in the step (2) was immediately, without being denatured, applied to the sample application zone on the test strip prepared in the step (5) to perform detection by chromatography. A colored line specific to the target nucleic acid was detected along the test line for the sample prepared using pUC19 as an analyte in the step (2). In contrast, there was no line detected for the negative control prepared using water instead. The detection by chromatography took as short a time as 10 to 15 minutes.

Example 3

(1) Synthesis of Artificial Nucleic Acid (Azobenzene)-Inserted Primers

In the same manner as in the step (1) in Example 1, a forward primer (F) and a reverse primer (R) were designed to be able to amplify about 330 base pairs by PCR amplification using pUC19 (available from Takara Bio, Inc.) as a template. Then, a polymerase reaction inhibitory region (X) containing azobenzene (artificial nucleic acid) and a tag sequence T5 or T6 were introduced into the 5' end of each corresponding primer to synthesize tagged primers T5-X-F and T6-X-R. These two azobenzene-inserted primers were purchased as products custom-synthesized by TSUKUBA OLIGO SERVICE CO., LTD. The following shows the primer set prepared in this study.

```
Tag sequence T5:
                                   (SEQ ID No: 16)
5'-Dd(TGGCAACATTTTTCACTGGGTTTATAG)-3'

Tag sequence T6:
                                   (SEQ ID No: 17)
5'-Dd(GGTTAGCTTCCAACCACGTGTAGATCA)-3'

Primer T5-X-F:
                                   (SEQ ID No: 18)
5'-Dd(TGGCAACATTTTTCACTGGGTTTATAG X
GGAAACAGCTATGACCATGA)-3'

Primer T6-X-R:
                                   (SEQ ID No: 19)
5'-Dd(GGTTAGCTTCCAACCACGTGTAGATCA X
TCTATGCGGCATCAGAGCAG)-3'
```

The azobenzene inserted into the primers is represented by the following formula (1).

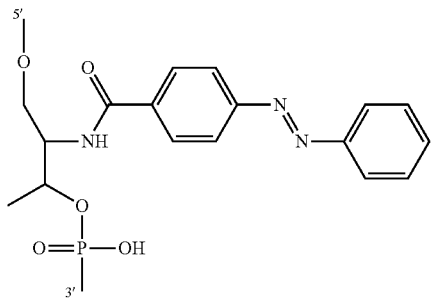

(1)

(2) PCR Using Azobenzene-Inserted Primer Set

PCR was performed using the primer set prepared by performing the above step (1). Specifically, a 100 μl PCR mixture was prepared by putting the primer T5-X-F and primer T6-X-R (15 pmol each) and pUC19 (10 ng) in a 0.2-ml PCR tube, and following the instruction manual of a PCR device ExTaq (available from Takara Bio, Inc.). Thereafter, the tube was set in a thermal cycler (GeneAmp PCR System, available from Applied Biosystems), and subjected to heat treatment at 95° C. for five minutes and then exposed to 35 cycles of 95° C. for 30 seconds, 55° C. for 30 seconds, and 72° C. for 30 seconds. Consequently, the target fragment of about 330 bp was amplified. Separately, the same reaction was carried out in the absence of pUC19 as a negative control.

(3) Preparation of Latex-Bound Oligonucleotide Probe

A carboxyl group-containing polystyrene latex (solids content: 10% (w/w), available from Bangs Laboratories, Inc.) and an amino-group containing oligonucleotide probe (SEQ ID No: 20, strand complementary to SEQ ID No: 16) were bonded by mixing them in MES buffer containing a necessary amount of a water-soluble carbodiimide, and the resulting product was blocked with monoethanolamine. The reaction solution was centrifuged, and the supernatant was then removed. The obtained precipitate was washed with water, and then resuspended in HEPES buffer with a surfactant. The suspension was uniformly applied to a glass fiber pad, and the pad was dried in a vacuum oven. In this manner, a conjugate pad was obtained.

```
Oligonucleotide probe 5:
                                   (SEQ ID No: 20)
5'-Dd(CTATAAACCCAGTGAAAAATGTTGCCA)-NH2-3'
```

(4) Immobilization of Oligonucleotide Probe on Solid Phase

A nylon membrane modified with carboxyl groups (available from Pall Corporation, 6 mm×60 mm) was treated with a water-soluble carbodiimide, and washed with deionized water. An amino group-containing D-oligonucleotide probe having a sequence (SEQ ID No: 21) complementary to SEQ ID No: 17 was applied to the activated membrane with a dispenser along a line drawn 30 mm from one end of the membrane, and air-dried for 15 minutes. Subsequently, the membrane was treated with Tris buffer and blocked, and then washed with water and dried.

```
Oligonucleotide probe 6:
                                   (SEQ ID No: 21)
5'-Dd(GATCATACACGTGGTTGGAAGCTAACC)-NH2-3'
```

(5) Preparation of Nucleic Acid Chromatography-Like Test Strip

A test strip to be used for detection of the PCR product amplified using the azobenzene-inserted primer set was prepared by attaching a chromatographic medium consisting of the nylon membrane prepared above, the conjugate pad prepared above, a general sample pad as a sample application zone, and an absorption pad for absorbing the developed sample and the labeling substance to a substrate consisting of a backing sheet as shown in FIG. 6.

(6) Detection of PCR Product Using Test Strip

The PCR product obtained in the step (2) was immediately, without being denatured, applied to the sample application zone on the test strip prepared in the step (5) to perform detection by chromatography. A colored line specific to the target nucleic acid was detected along the test line for the sample prepared using pUC19 as an analyte in the step (2). In contrast, there was no line detected for the negative control prepared using water instead. The detection by chromatography took as short a time as 10 to 15 minutes.

Example 4

(1) Preparation of Gold Colloid-Bound Oligonucleotide Probe

Gold Colloid (40 nm, 9.0×10¹⁰ (particles/ml), available from British BioCell International) and a thiol group-containing oligonucleotide probe (SEQ ID No: 22, strand complementary to SEQ ID No: 16) were mixed and incubated at 50° C. for 16 hours. The resulting mixture was centrifuged at 6000 rpm for 15 minutes, and the supernatant was removed. The residue was combined and mixed with 0.05 M sodium chloride and 5 mM phosphate buffer (pH 7), and then incubated again at 50° C. for 40 hours.

After the incubation, the resulting mixture was centrifuged (6000 rpm, 15 minutes). The supernatant was removed, and the residue was combined with 5 mM phosphate buffer (pH 7). This buffer replacement procedure was performed again.

The obtained gold colloid solution was uniformly applied to a glass fiber pad, and the pad was dried in a vacuum oven. In this manner, a conjugate pad was obtained.

```
Oligonucleotide probe 7:
                                         (SEQ ID No: 22)
5'-Dd(CTATAAACCCAGTGAAAAATGTTGCCA)-SH-3'
```

(2) Immobilization of Oligonucleotide Probe on Solid Phase

A 3'-biotin-modified oligonucleotide probe having a sequence (SEQ ID No: 23) complementary to SEQ ID No: 17 was mixed with streptavidin. The resulting mixture was applied along a line on a nitrocellulose membrane (product name: Hi-Flow 180, available from Millipore Corporation) with a dispenser, and air-dried at 40° C. for 30 minutes.

```
Oligonucleotide probe 8:
                                         (SEQ ID No: 23)
5'-Dd(GATCATACACGTGGTTGGAAGCTAACC)-Biotin-3'
```

(3) Preparation of Nucleic Acid Chromatography-Like Test Strip

A test strip to be used for detection of the PCR product amplified using the azobenzene-inserted primer set was prepared by attaching a chromatographic medium consisting of the nitrocellulose membrane prepared above, the conjugate pad prepared above, a general sample pad as a sample application zone, and an absorption pad for absorbing the developed sample and the labeling substance to a substrate consisting of a backing sheet as shown in FIG. 6.

(4) Detection of PCR Product Using Test Strip

The PCR product obtained in the step (2) in Example 3 was immediately, without being denatured, applied to the sample application zone on the test strip prepared in the step (3) to perform detection by chromatography. A colored line specific to the target nucleic acid was detected along the test line for the sample prepared using pUC19 as an analyte in the step (2) in Example 3. In contrast, there was no line detected for the negative control prepared using water instead. The detection by chromatography took as short a time as 10 to 15 minutes.

Example 5

(1) Immobilization of Oligonucleotide Probe on Solid Phase

An oligonucleotide probe having a sequence (SEQ ID No: 24) complementary to SEQ ID No: 17 was applied along a line on an UltraBind affinity membrane (available from Pall Corporation) with a dispenser, and air-dried at 80° C. for one hour.

```
Oligonucleotide probe 9:
                                         (SEQ ID No: 24)
5'-Dd(GATCATACACGTGGTTGGAAGCTAACC)-3'
```

(2) Preparation of Nucleic Acid Chromatography-Like Test Strip

A test strip to be used for detection of the PCR product amplified using the azobenzene-inserted primer set was prepared by attaching a chromatographic medium consisting of the UltraBind affinity membrane prepared above, the conjugate pad prepared above, a general sample pad as a sample application zone, and an absorption pad for absorbing the developed sample and the labeling substance to a substrate consisting of a backing sheet as shown in FIG. 6.

(3) Detection of PCR Product Using Test Strip

The PCR product obtained in the step (2) in Example 3 was immediately, without being denatured, applied to the sample application zone on the test strip prepared in the step (2) to perform detection by chromatography. A colored line specific to the target nucleic acid was detected along the test line for the sample prepared using pUC19 as an analyte in the step (2) in Example 3. In contrast, there was no line detected for the negative control prepared using water instead. The detection by chromatography took as short a time as 10 to 15 minutes.

Example 6

(1) Synthesis of Artificial Nucleic Acid (Azobenzene)-Inserted Primers

In this example, three pairs of primers, a forward primer (F1) and a reverse primer (R1), a forward primer (F2) and a reverse primer (R2), and a forward primer (F3) and a reverse primer (R3), were designed to be able to amplify about 330 base pairs, about 200 base pairs, and about 100 base pairs, respectively, by PCR amplification using the three genes: pUC19 (available from Takara Bio, Inc.), an EcoRI methylase gene, and a BamHI methylase gene as target nucleic acid templates, respectively. Then, a polymerase reaction inhibitory region (X) containing azobenzene (artificial nucleic acid) and a tag sequence T10 or T11, or a tag sequence T12 or T13, or a tag sequence T14 or T15 were introduced into the 5' end of each corresponding primer to synthesize tagged primers T10-X-F1 and T11-X-R1, T12-X-F2 and T13-X-R2, and T14-X-F3 and T15-X-R3. These six azobenzene-inserted primers were purchased as products custom-synthesized by TSUKUBA OLIGO SERVICE CO., LTD. The following shows the three primer sets prepared in this study.

```
Tag sequence T10:
                                         (SED ID No: 25)
5'-Dd(TGGCAACATTTTTCACTGGGTTTATAG)-3'

Tag sequence T11:
                                         (SEQ ID No: 26)
5'-Dd(GGTTAGCTTCCAACCACGTGTAGATCA)-3'

Primer T10-X-F1:
                                         (SEQ ID No: 27)
5'-Dd(TGGCAACATTTTTCACTGGGTTTATAG X
GGAAACAGCTATGACCATGA)-3'

Primer T11-X-R1:
                                         (SEQ ID No: 28)
5'-Dd(GGTTAGCTTCCAACCACGTGTAGATCA X
TCTATGCGGCATCAGAGCAG)-3'

Tag sequence T12:
                                         (SEQ ID No: 29)
5'-Dd(CGCATTGAGCAAGTGTACAGAGCAT)-3'

Tag sequence T13:
                                         (SEQ ID No: 30)
5'-Dd(ATTATGCGTGGAGAAGCATATCATA)-3'

Primer T12-X-F2:
                                         (SEQ ID No: 31)
5'-Dd(CGCATTGAGCAAGTGTACAGAGCAT X
AGCATTATGAATTATATGGT)-3'
```

-continued

Primer T13-X-R2:
(SEQ ID No: 32)
5'-Dd(ATTATGCGTGGAGAAGCATATCATA X
TTGTTTACATTTATAGCATC)-3'

Tag sequence T14:
(SEQ ID No: 33)
5'-Dd(AATTGCGCATGTCCATGTGTAA)-3'

Tag sequence T15:
(SEQ ID No: 34)
5'-Dd(TACTTTAGAGGAAACTGCTGAG)-3'

Primer T14-X-F3:
(SEQ ID No: 35)
5'-Dd(AATTGCGCATGTCCATGTGTAA X
TGGTTTTAAAACTCTGATAC)-3'

Primer T15-X-R3:
(SEQ ID No: 36)
5'-Dd(TACTTTAGAGGAAACTGCTGAG X
AGTATGATGAGGGTGTAACA)-3'

(2) PCR Using Three Azobenzene-Inserted Primer Sets

PCR was performed using the three primer sets prepared by performing the above step (1). Specifically, a 100 μl PCR mixture was prepared by putting the primer T10-X-F1 and primer T11-X-R1, the primer T12-X-F2 and primer T13-X-R2, and the primer T14-X-F3 and primer T15-X-R3 (15 pmol each) and the template(s) (10 ng each) in a 0.2-ml PCR tube, and following the instruction manual of a PCR device ExTaq (available from Takara Bio, Inc.). The following five kinds of PCR mixtures were prepared:
(i) a PCR mixture containing pUC19 (available from Takara Bio, Inc.) as a template;
(ii) a PCR mixture containing the EcoRI methylase gene as a template;
(iii) a PCR mixture containing the BamHI methylase gene as a template;
(iv) a PCR mixture containing all the three templates pUC19 (available from Takara Bio, Inc.), the EcoRI methylase gene, and the BamHI methylase gene; and
(v) a PCR mixture containing no template.

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Consequently, the following DNA fragments containing the target sequences were amplified: (i) about 330 bp; (ii) about 200 bp; (iii) about 100 bp; (iv) three fragments of about 330 bp, about 200 bp, and about 100 bp; and (v) no amplified DNA fragment (negative control).

(3) Preparation of Latex-Bound Oligonucleotide Probes

Each pair of a carboxyl group-containing polystyrene latex (blue) (solids content: 10% (w/w), available from Bangs Laboratories, Inc.) and an amino group-containing oligonucleotide probe 16 (SEQ ID No: 37, strand complementary to SEQ ID No: 25), a carboxyl group-containing polystyrene latex (orange) (solids content: 10% (w/w), available from Bangs Laboratories, Inc.) and an amino group-containing oligonucleotide probe 17 (SEQ ID No: 38, strand complementary to SEQ ID No: 29), and a carboxyl group-containing polystyrene latex (green) (solids content: 10% (w/w), available from Bangs Laboratories, Inc.) and an amino group-containing oligonucleotide probe 18 (SEQ ID No: 39, strand complementary to SEQ ID No: 33) were bonded by mixing the pair in MES buffer containing a necessary amount of a water-soluble carbodiimide, and the resulting products were blocked with monoethanolamine. The reaction solutions were centrifuged, and the supernatants were then removed. The obtained precipitates were individually washed with water and then resuspended in HEPES buffer with a surfactant to prepare an oligonucleotide probe 16-bound latex (blue), an oligonucleotide probe 17-bound latex (orange), and an oligonucleotide probe 18-bound latex (green), respectively.

These three latexes were uniformly applied to a glass fiber pad, and the pad was dried in a vacuum oven. In this manner, a conjugate pad was obtained.

Oligonucleotide probe 16:
(SEQ ID No: 37)
5'-Dd(CTATAAACCCAGTGAAAAATGTTGCCA)-NH2-3'

Oligonucleotide probe 17:
(SEQ ID No: 38)
5'-Dd(TTGCTCTGTACACTTGCTCAATGCG)-NH2-3'

Oligonucleotide probe 18:
(SEQ ID No: 39)
5'-Dd(TTACACATGGACATGCGCAATT)-NH2-3'

(4) Immobilization of Three Oligonucleotide Probes on Solid Phase

A 3'-biotin-modified oligonucleotide probe having a sequence (SEQ ID No: 40) complementary to SEQ ID No: 26, a 3'-biotin-modified oligonucleotide probe having a sequence (SEQ ID No: 41) complementary to SEQ ID No: 30, and a 3'-biotin-modified oligonucleotide probe having a sequence (SEQ ID No: 42) complementary to SEQ ID No: 34 were individually mixed with streptavidin. The resulting mixtures were applied with a dispenser respectively along three separated lines on a nitrocellulose membrane (product name: Hi-Flow 135, available from Millipore Corporation) in the stated order from the upstream, and air-dried at 40° C. for 30 minutes. In this manner, three detection lines were formed.

Oligonucleotide probe 19:
(SEQ ID No: 40)
5'-Dd(GATCATACACGTGGTTGGAAGCTAACC)-Biotin-3'

Oligonucleotide probe 20:
(SEQ ID No: 41)
5'-Dd(TATGATATGCTTCTCCACGCATAAT)-Biotin-3'

Oligonucleotide probe 21:
(SEQ ID No: 42)
5'-Dd(CTCAGCAGTTTCCTCTAAAGTA)-Biotin-3'

(5) Preparation of Nucleic Acid Chromatography-Like Test Strip

A test strip to be used for detection of the PCR products amplified using the azobenzene-inserted primer sets was prepared by attaching a chromatographic medium consisting of the nitrocellulose membrane prepared above, the conjugate pad prepared in the step (3), a general sample pad as a sample application zone, and an absorption pad for absorbing the developed sample and the labeling substances to a substrate consisting of a backing sheet as shown in FIG. 6.

(6) Detection of PCR Products Using Test Strip

Each of the PCR products (i) to (v) prepared in the step (2) was immediately, without being denatured, applied to the sample application zone on the test strip prepared in the step (5) to perform detection by chromatography. The results are shown below.
(i): Only the first detection line turned blue.
(ii): Only the second detection line turned orange.

(iii): Only the third detection line turned green.
(iv): The first, second, and third detection lines turned blue, orange, and green, respectively.
(v): No color change was observed for all the detection lines.

The results confirmed that it is possible to specifically detect each of the target genes and to simultaneously detect the three kinds of genes.

The detection by chromatography took as short a time as 10 to 15 minutes.

Example 7

(1) Synthesis of Joint Primers

In this example, three pairs of primers, a forward primer (Fj1) and a reverse primer (Rj1), a forward primer (Fj2) and a reverse primer (Rj2), and a forward primer (Fj3) and a reverse primer (Rj3)), were designed to be able to amplify about 330 base pairs, about 200 base pairs, and about 100 base pairs, respectively, by PCR amplification using the three genes: pUC19 (available from Takara Bio, Inc.), an EcoRI methylase gene, and a BamHI methylase gene as target nucleic acid templates, respectively. Then, common sequences KF1 and KR1, common sequences KF2 and KR2, or common sequences KF3 and KR3 were introduced into the 5' ends of each corresponding primer pair to synthesize common sequence-added primers KF1-Fj1 and KR1-Rj1, KF2-Fj2 and KR2-Rj2, and KF3-Fj3 and KR3-Rj3. These six common sequence-added primers (joint primers) were purchased as products custom-synthesized by TSUKUBA OLIGO SERVICE CO., LTD. The following shows the three primer sets prepared in this study.

Common sequence KF1:
(SEQ ID No: 43)
5'-$^D$d(TGGGCTGACCTAGAGGTCTT)-3'

Common sequence KR1:
(SEQ ID No: 44)
5'-$^D$d(ATGAAATGCAGGCCATTCGG)-3'

Primer KF1-Rj1:
(SEQ ID No: 45)
5'-$^D$d(TGGGCTGACCTAGAGGTCTT
GGAAACAGCTATGACCATGA)-3'

Primer KR1-Rj1:
(SEQ ID No: 46)
5'-$^D$d(ATGAAATGCAGGCCATTCGG
TCTATGCGGCATCAGAGCAG)-3'

Common sequence KF2:
(SEQ ID No: 47)
5'-$^D$d(CCGGAACAGACACCAGGTTT)-3'

Common sequence KR2:
(SEQ ID No: 48)
5'-$^D$d(GAAGCTGTACCGTCACATGA)-3'

Primer KF2-Fj2:
(SEQ ID No:49)
5'-$^D$d(CCGGAACAGACACCAGGTTT
AGCATTATGAATTATATGGT)-3'

Primer KR2-Rj2:
(SEQ ID No: 50)
5'-$^D$d(GAAGCTGTACCGTCACATGA
TTGTTTACATTTATAGCATC)-3'

Common sequence KF3:
(SEQ ID No: 51)
5'-$^D$d(ATACCGATGAGTGTGCTACC)-3'

Common sequence KR3:
(SEQ ID No: 52)
5'-$^D$d(TGGCCTGTGTGACACTATGC)-3'

Primer KF3-Fj3:
(SEQ ID No: 53)
5'-$^D$d(ATACCGATGAGTGTGCTACC
TGGTTTTAAAACTCTGATAC)-3'

Primer KR3-Rj3:
(SEQ ID No: 54)
5'-$^D$d(TGGCCTGTGTGACACTATGC
AGTATGATGAGGGTGTAACA)-3'

(2) Synthesis of Artificial Nucleic Acid (Azobenzene)-Inserted Primers

In this example, three pairs of primers containing the same common sequences as those of the respective joint primers prepared in the step 1 were designed to be able to respectively bind to the three kinds of PCR fragments amplified respectively using the joint primer sets. Then, a polymerase reaction inhibitory region (X) containing azobenzene (artificial nucleic acid) and a tag sequence T22 or T23, or a tag sequence T24 or T25, or a tag sequence T26 or T27 were introduced into the 5' end of each corresponding primer to synthesize tagged primers T22-X-KF1 and T23-X-KR1, T24-X-KF2 and T25-X-KR2, and T26-X-KF3 and T27-X-KR3. These six azobenzene-inserted primers were purchased as products custom-synthesized by TSUKUBAO-LIGO SERVICE CO., LTD. The following shows the three primer sets prepared in this study.

Tag sequence T22:
(SEQ ID No: 55)
5'-$^D$d(TGGCAACATTTTTCACTGGGTTTATAG)-3'

Tag sequence T23:
(SEQ ID No: 56)
5'-$^D$d(GGTTAGCTTCCAACCACGTGTAGATCA)-3'

Primer T22-X-KF1:
(SEQ ID No: 57)
5'-$^D$d(TGGCAACATTTTTCACTGGGTTTATAG X
TGGGCTGACCTAGAGGTCTT)-3'

Primer T23-X-KR1:
(SEQ ID No: 58)
5'-$^D$d(GGTTAGCTTCCAACCACGTGTAGATCA X
ATGAAATGCAGGCCATTCGG)-3'

Tag sequence T24:
(SEQ ID No: 59)
5'-$^D$d(CGCATTGAGCAAGTGTACAGAGCAT)-3'

Tag sequence T25:
(SEQ ID No: 60)
5'-$^D$d(ATTATGCGTGGAGAAGCATATCATA)-3'

Primer T24-X-KF2:
(SEQ ID No: 61)
5'-$^D$d(CGCATTGAGCAAGTGTACAGAGCAT X
CCGGAACAGACACCAGGTTT)-3'

Primer T25-X-KR2:
(SEQ ID No: 62)
5'-$^D$d(ATTATGCGTGGAGAAGCATATCATA X
GAAGCTGTACCGTCACATGA)-3'

Tag sequence T26:
(SEQ ID No: 63)
5'-$^D$d(AATTGCGCATGTCCATGTGTAA)-3'

-continued

Tag sequence T27:
(SEQ ID No: 64)
5'-$^D$d(TACTTTAGAGGAAACTGCTGAG)-3'

Primer T26-X-KF3:
(SEQ ID No: 65)
5'-$^D$d(AATTGCGCATGTCCATGTGTAA X
ATACCGATGAGTGTGCTACC)-3'

Primer T27-X-KR3:
(SEQ ID No: 66)
5'-$^D$d(TACTTTAGAGGAAACTGCTGAG X
TGGCCTGTGTGACACTATGC)-3'

(3) PCR Using Joint Primers and Azobenzene-Inserted Primers

PCR was performed using the six primer sets prepared by performing the above steps (1) and (2). Specifically, a 100 µl PCR mixture was prepared by putting the primer KF1-Fj1, the primer KR1-Rj1, the primer KF2-Fj2, the primer KR2-Rj2, the primer KF3-Fj3, the primer KR3-Rj3, the primer T22-X-KF1, the primer T23-X-KR1, the primer T24-X-KF2, the primer T25-X-KR2, the primer T26-X-KF3, and the primer T27-X-KR3 (8 pmol each), and the template(s) (10 ng each) in a 0.2-ml PCR tube, according to the instruction manual of a PCR device ExTaq (available from Takara Bio, Inc.). The following five kinds of PCR mixtures were prepared:
(i) a PCR mixture containing pUC19 (available from Takara Bio, Inc.) as a template;
(ii) a PCR mixture containing the EcoRI methylase gene as a template;
(iii) a PCR mixture containing the BamHI methylase gene as a template;
(iv) a PCR mixture containing all the three templates pUC19 (available from Takara Bio, Inc.), the EcoRI methylase gene, and the BamHI methylase gene; and
(v) a PCR mixture containing no template.

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Consequently, the following DNA fragments containing the target sequences were amplified: (i) about 360 bp; (ii) about 230 bp; (iii) about 130 bp; (iv) three fragments of about 360 bp, about 230 bp, and about 130 bp; and (v) no amplified DNA fragment (negative control).

(4) Preparation of Latex-Bound Oligonucleotide Probes

Each pair of a carboxyl group-containing polystyrene latex (blue) (solids content: 10% (w/w), available from Bangs Laboratories, Inc.) and an amino group-containing oligonucleotide probe 28 (SEQ ID No: 67, strand complementary to SEQ ID No: 55), a carboxyl group-containing polystyrene latex (orange) (solids content: 10% (w/w), available from Bangs Laboratories, Inc.) and an amino group-containing oligonucleotide probe 29 (SEQ ID No: 68, strand complementary to SEQ ID No: 59), and a carboxyl group-containing polystyrene latex (green) (solids content: 10% (w/w), available from Bangs Laboratories, Inc.) and an amino group-containing oligonucleotide probe 30 (SEQ ID No: 69, strand complementary to SEQ ID No: 63) were bonded by mixing the pair in MES buffer containing a necessary amount of a water-soluble carbodiimide, and the resulting products were blocked with monoethanolamine. The reaction solutions were centrifuged, and the supernatants were then removed. The obtained precipitates were individually washed with water and then resuspended in HEPES buffer with a surfactant to prepare an oligonucleotide probe 28-bound latex (blue), an oligonucleotide probe 29-bound latex (orange), and an oligonucleotide probe 30-bound latex (green), respectively.

These three latexes were uniformly applied to a glass fiber pad, and the pad was dried in a vacuum oven. In this manner, a conjugate pad was obtained.

Oligonucleotide probe 28:
(SEQ ID No: 67)
5'-$^D$d(CTATAAACCCAGTGAAAAATGTTGCCA)-NH$_2$-3'

Oligonucleotide probe 29:
(SEQ ID No: 68)
5'-$^D$d(TTGCTCTGTACACTTGCTCAATGCG)-NH$_2$-3'

Oligonucleotide probe 30:
(SEQ ID No: 69)
5'-$^D$d(TTACACATGGACATGCGCAATT)-NH$_2$-3'

(5) Immobilization of Three Oligonucleotide Probes on Solid Phase

A 3'-biotin-modified oligonucleotide probe having a sequence (SEQ ID No: 70) complementary to SEQ ID No: 56, a 3'-biotin-modified oligonucleotide probe having a sequence (SEQ ID No: 71) complementary to SEQ ID No: 60, and a 3'-biotin-modified oligonucleotide probe having a sequence (SEQ ID No: 72) complementary to SEQ ID No: 64 were individually mixed with streptavidin. The resulting mixtures were applied with a dispenser respectively along three separated lines on a nitrocellulose membrane (product name: Hi-Flow 135, available from Millipore Corporation) in the stated order from the upstream, and air-dried at 40° C. for 30 minutes. In this manner, three detection lines were formed.

Oligonucleotide probe 31:
(SEQ ID No: 70)
5'-$^D$d(GATCATACACGTGGTTGGAAGCTAACC)-Biotin-3'

Oligonucleotide probe 32:
(SEQ ID No: 71)
5'-$^D$d(TATGATATGCTTCTCCACGCATAAT)-Biotin-3'

Oligonucleotide probe 33:
(SEQ ID No: 72)
5'-$^D$d(CTCAGCAGTTTCCTCTAAAGTA)-Biotin-3'

(6) Preparation of Nucleic Acid Chromatography-Like Test Strip

A test strip to be used for detection of the PCR products amplified using the azobenzene-inserted primer sets was prepared by attaching a chromatographic medium consisting of the nitrocellulose membrane prepared above, the conjugate pad prepared in the step (4), a general sample pad as a sample application zone, and an absorption pad for absorbing the developed sample and the labeling substances to a substrate consisting of a backing sheet as shown in FIG. 6.

(7) Detection of PCR Products Using Test Strip

Each of the PCR products (i) to (v) prepared in the step (3) was immediately, without being denatured, applied to the sample application zone on the test strip prepared in the step (6) to perform detection by chromatography. The results are shown below.
(i): Only the first detection line turned blue.
(ii): Only the second detection line turned orange.
(iii): Only the third detection line turned green.
(iv): The first, second, and third detection lines turned blue, orange, and green, respectively.
(v): No color change was observed for all the detection lines.

The results confirmed that it is possible to specifically detect each of the target genes and to detect the three kinds of genes. The detection by chromatography took as short a time as 10 to 15 minutes.

Example 8

(1) Synthesis of Joint Primer

In this example, a forward primer (F) and a reverse primer (R) were designed to be able to amplify about 330 base pairs by PCR amplification using pUC19 (available from Takara Bio, Inc.) as a target nucleic acid template. Then, common sequences KF and KR were respectively introduced into the 5' ends of these primers to synthesize common sequence-added primers KF-F and KR-R. These two common sequence-added primers (joint primers) were purchased as products custom-synthesized by TSUKUBA OLIGO SERVICE CO., LTD. The following shows the primer set prepared in this study.

```
Common sequence KF:
                                       (SEQ ID No: 73)
5'-Dd(TGGGCTGACCTAGAGGTCTT)-3'

Common sequence KR:
                                       (SEQ ID No: 74)
5'-Dd(ATGAAATGCAGGCCATTCGG)-3'

Primer KF-F:
                                       (SEQ ID No: 75)
5'-Dd(TGGGCTGACCTAGAGGTCTT
GGAAACAGCTATGACCATGA)-3'

Primer KR-R:
                                       (SEQ ID No: 76)
5'-Dd(ATGAAATGCAGGCCATTCGG
TCTATGCGGCATCAGAGCAG)-3'
```

(2) Synthesis of Biotin-Modified Primer and FITC-Modified Primer

In this example, primers containing the same common sequences as those of the respective joint primers prepared in the step (1) were designed to be able to bind to the PCR fragment amplified using the joint primer set. One of these primers synthesized had a 5' end modified with biotin, and the other had a 5' end modified with FITC. These two modified primers were purchased as products custom-synthesized by TSUKUBA OLIGO SERVICE CO., LTD. The following shows the primer set prepared in this study.

```
Primer KF2:
                                       (SEQ ID No: 77)
5'-Biotin-Dd(TGGGCTGACCTAGAGGTCTT)-3'

Primer KR2:
                                       (SEQ ID No: 78)
5'-FITC-Dd(ATGAAATGCAGGCCATTCGG)-3'
```

(3) PCR Using Joint Primer and Modified Primer

PCR was performed using the primer sets prepared by performing the above steps (1) and (2). Specifically, a 100 µl PCR mixture was prepared by putting the primer KF-F, the primer KR-R, the primer KF2, and the primer KR2 (8 pmol each), and pUC19 (10 ng) as a template in a 0.2-ml PCR tube, and following the instruction manual of a PCR device ExTaq (available from Takara Bio, Inc.). After the preparation of the PCR mixture, the tube was set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Consequently, an about 360-bp DNA fragment containing the target sequence was amplified.

(4) Preparation of Latex-Bound Streptavidin

A carboxyl group-containing polystyrene latex (blue) (solids content: 10% (w/w), available from Bangs Laboratories, Inc.) and streptavidin (available from Wako Pure Chemical Industries, Ltd.) were bonded by mixing them in MES buffer containing a necessary amount of a water-soluble carbodiimide, and the resulting product was blocked with monoethanolamine. The reaction solution was centrifuged, and the supernatant was then removed. The obtained precipitate was washed with water, and then resuspended in HEPES buffer with a surfactant to prepare a streptavidin-bound latex (blue). This latex solution was uniformly applied to a glass fiber pad, and the pad was dried in a vacuum oven. In this manner, a conjugate pad was obtained.

(5) Immobilization of Anti-FITC (Fluorescein Isothiocyanate) Antibody to Solid Phase An anti-FITC antibody (available from Invitrogen) was dissolved in 5 mM Tris buffer (pH 7.5), and applied with a dispenser along a line on a nitrocellulose membrane (product name: Hi-Flow 135, available from Millipore Corporation), and then air-dried at 40° C. for 30 minutes. In this manner, a detection line was formed.

(6) Preparation of Nucleic Acid Chromatography-Like Test Strip

A test strip to be used for detection of the PCR product amplified using the set of the biotin-modified primer and the FITC-modified primer was prepared by attaching a chromatographic medium consisting of the nitrocellulose membrane prepared above, the conjugate pad prepared in the step (4), a general sample pad as a sample application zone, and an absorption pad for absorbing the developed sample and the labeling substance to a substrate consisting of a backing sheet as shown in FIG. 6.

(7) Detection of PCR Product Using Test Strip

The PCR product obtained in the step (3) was immediately, without being denatured, applied to the sample application zone on the test strip prepared in the step (6) to perform detection by chromatography. Consequently, a colored line specific to the target nucleic acid was detected along the test line for the sample prepared using pUC19 as an analyte in the step (3). In contrast, there was no line detected for the negative control prepared using water instead. The detection by chromatography took as short a time as 10 to 15 minutes.

Example 9

(1) Synthesis of Joint Primers

In this example, three pairs of primers, a forward primer (Fj1) and a reverse primer (Rj1), a forward primer (Fj2) and a reverse primer (Rj2), and a forward primer (Fj3) and a reverse primer (Rj3), were designed to be able to amplify about 330 base pairs, about 200 base pairs, and about 100 base pairs, respectively, by PCR amplification using the three genes: pUC19 (available from Takara Bio, Inc.), an EcoRI methylase gene, and a BamHI methylase gene as target nucleic acid templates, respectively. Then, common sequences KF1 and KR1, common sequences KF2 and KR2, or common sequences KF3 and KR3 were introduced into the 5' ends of each corresponding primer pair to synthesize common sequence-added primers KF1-Fj1 and KR1-Rj1, KF2-Fj2 and KR2-Rj2, and KF3-Fj3 and KR3-Rj3. These six common sequence-added primers (joint primers) were purchased as products custom-synthesized by TSUKUBA OLIGO SERVICE CO., LTD. The following shows the three primer sets prepared in this study.

```
Common sequence KF1:
                                    (SEQ ID No: 79)
5'-Dd(TGGGCTGACCTAGAGGTCTT)-3'

Common sequence KR1:
                                    (SEQ ID No: 80)
5'-Dd(ATGAAATGCAGGCCATTCGG)-3'

Primer KF1-Fj1:
                                    (SEQ ID No: 81)
5'-Dd(TGGGCTGACCTAGAGGTCTT
GGAAACAGCTATGACCATGA)-3'

Primer KR1-Rj1:
                                    (SEQ ID No: 82)
5'-Dd(ATGAAATGCAGGCCATTCGG
TCTATGCGGCATCAGAGCAG)-3'

Common sequence KF2:
                                    (SEQ ID No: 83)
5'-Dd(CCGGAACAGACACCAGGTTT)-3'

Common sequence KR2:
                                    (SEQ ID No: 84)
5'-Dd(GAAGCTGTACCGTCACATGA)-3'

Primer KF2-Fj2:
                                    (SEQ ID No: 85)
5'-Dd(CCGGAACAGACACCAGGTTT
AGCATTATGAATTATATGGT)-3'

Primer KR2-Rj2:
                                    (SEQ ID No: 86)
5'-Dd(GAAGCTGTACCGTCACATGA
TTGTTTACATTTATAGCATC)-3'

Common sequence KF3:
                                    (SEQ ID No: 87)
5'-Dd(ATACCGATGAGTGTGCTACC)-3'

Common sequence KR3:
                                    (SEQ ID No: 88)
5'-Dd(TGGCCTGTGTGACACTATGC)-3'

Primer KF3-Fj3:
                                    (SEQ ID No: 89)
5'-Dd(ATACCGATGAGTGTGCTACC
TGGTTTTAAAACTCTGATAC)-3'

Primer KR3-Rj3:
                                    (SEQ ID No: 90)
5'-Dd(TGGCCTGTGTGACACTATGC
AGTATGATGAGGGTGTAACA)-3'
```

(2) Synthesis Of Artificial Nucleic Acid (Azobenzene)-Inserted Primers and Biotin-Modified Primers In this example, three pairs of primers containing the same common sequences as those of the respective joint primers prepared in the step (1) were designed to be able to respectively bind to the three kinds of PCR fragments amplified respectively using the joint primer sets. As one primer of each of these three pairs, primers modified with biotin at the 5' end, i.e., KF1, KF2 and KF3, were synthesized. Also, as the other primer of each of these three pairs, tagged primers having at the 5' end a polymerase reaction inhibitory region (X) containing azobenzene (artificial nucleic acid), and a tag sequence T34, T35 or T36, i.e., T34-X-KR1, T35-X-KR2, and T36-X-KR3, were synthesized. These six modified primers were purchased as products custom-synthesized by TSUKUBA OLIGO SERVICE CO., LTD. The following shows the three primer sets prepared.

```
Tag sequence T34:
                                    (SEQ ID No: 91)
5'-Dd(GGTTAGCTTCCAACCACGTGTAGATCA)-3'

Primer KF1:
                                    (SEQ ID No: 92)
5'-Biotin-Dd(TGGGCTGACCTAGAGGTCTT)-3'

Primer T34-X-KR1:
                                    (SEQ ID No: 93)
5'-Dd(GGTTAGCTTCCAACCACGTGTAGATCA X
ATGAAATGCAGGCCATTCGG)-3'

Tag sequence T35:
                                    (SEQ ID No: 94)
5'-Dd(ATTATGCGTGGAGAAGCATATCATA)-3'

Primer KF2:
                                    (SEQ ID No: 95)
5'-Biotin-Dd(CCGGAACAGACACCAGGTTT)-3'

Primer T35-X-KR2:
                                    (SEQ ID No: 96)
5'-Dd(ATTATGCGTGGAGAAGCATATCATA X
GAAGCTGTACCGTCACATGA)-3'

Tag sequence T36:
                                    (SEQ ID No: 97)
5'-Dd(TACTTTAGAGGAAACTGCTGAG)-3'

Primer KF3:
                                    (SEQ ID No: 98)
5'-Biotin-Dd(ATACCGATGAGTGTGCTACC)-3'

Primer T36-X-KR3:
                                    (SEQ ID No: 99)
5'-Dd(TACTTTAGAGGAAACTGCTGAG X
TGGCCTGTGTGACACTATGC)-3'
```

(3) PCR Using Joint Primers and Azobenzene-Inserted Primers

PCR was performed using the six primer sets prepared by performing the above steps (1) and (2). Specifically, a 100 μl PCR mixture was prepared by putting the primer KF1-Fj1, the primer KR1-Rj1, the primer KF2-Fj2, the primer KR2-Rj2, the primer KF3-Fj3, the primer KR3-Rj3, the primer KF1, the primer T34-X-KR1, the primer KF2, the primer T35-X-KR2, the primer KF3, and the primer T36-X-KR3 (8 pmol each), and the template (s) (10 ng each) in a 0.2-ml PCR tube, and following the instruction manual of a PCR device ExTaq (available from Takara Bio, Inc.). The following five kinds of PCR mixtures were prepared:

(i) a PCR mixture containing pUC19 (available from Takara Bio, Inc.) as a template;

(ii) a PCR mixture containing the EcoRI methylase gene as a template;

(iii) a PCR mixture containing the BamHI methylase gene as a template;

(iv) a PCR mixture containing all the three templates pUC19 (available from Takara Bio, Inc.), the EcoRI methylase gene, and the BamHI methylase gene; and (v) a PCR mixture containing no template.

After these PCR mixtures were prepared, the tubes were set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Consequently, the following DNA fragments containing the target sequences were amplified: (i) about 360 bp; (ii) about 230 bp; (iii) about 130 bp; (iv) three fragments of about 360 bp, about 230 bp, and about 130 bp; and (v) no amplified DNA fragment (negative control).

(4) Preparation of Gold Colloid-Bound Streptavidin

Gold Colloid (particle size: 40 nm, available from British BioCell International) and streptavidin were mixed and incubated at 50° C. for 16 hours. The resulting mixture was centrifuged at 6000 rpm for 15 minutes, and the supernatant was removed. The residue was combined and mixed with 0.05 M sodium chloride and 5 mM phosphate buffer (pH 7), and then incubated again at 50° C. for 40 hours.

After the incubation, the resulting mixture was centrifuged (6000 rpm, 15 minutes). The supernatant was removed, and the residue was combined with 5 mM phosphate buffer (pH 7). This buffer replacement procedure was performed again.

The obtained gold colloid solution was uniformly applied to a glass fiber pad, and the pad was then dried in a vacuum oven. In this manner, a conjugate pad was obtained.

(5) Immobilization of Three Oligonucleotide Probes on Solid Phase

An oligonucleotide probe having a sequence (SEQ ID No: 100) complementary to SEQ ID No: 91, an oligonucleotide probe having a sequence (SEQ ID No: 101) complementary to SEQ ID No: 94, and an oligonucleotide probe having a sequence (SEQ ID No: 102) complementary to SEQ ID No: 97 were synthesized. The resulting probe solutions were applied with a dispenser respectively along three separated lines on a nitrocellulose membrane (product name: Hi-Flow 135, available from Millipore Corporation) in the stated order from the upstream, and air-dried at 40° C. for 30 minutes. In this manner, three detection lines were formed.

```
Oligonucleotide probe 37:
                                   (SEQ ID No: 100)
5'-Dd(GATCATACACGTGGTTGGAAGCTAACC)-3'

Oligonucleotide probe 38:
                                   (SEQ ID No: 101)
5'-Dd(TATGATATGCTTCTCCACGCATAAT)-3'

Oligonucleotide probe 39:
                                   (SEQ ID No: 102)
5'-Dd(CTCAGCAGTTTCCTCTAAAGTA)-3'
```

(6) Preparation of Nucleic Acid Chromatography-Like Test Strip

A test strip to be used for detection of the PCR products amplified using the sets of the biotin-modified primers and the azobenzene-inserted primers was prepared by attaching a chromatographic medium consisting of the nitrocellulose membrane prepared above, the conjugate pad prepared in the step (4), a general sample pad as a sample application zone, and an absorption pad for absorbing the developed sample and the labeling substance to a substrate consisting of a backing sheet as shown in FIG. 6.

(7) Detection of PCR Products Using Test Strip

Each of the PCR products (i) to (v) prepared in the step (3) was immediately, without being denatured, applied to the sample application zone on the test strip prepared in the step (6) to perform detection by chromatography. The results are shown below.

(i): Only the first detection line was colored.

(ii): Only the second detection line was colored.

(iii): Only the third detection line was colored.

(iv): All the first, second, and third detection lines were colored.

(v): No color change was observed for all the detection lines.

The results confirmed that it is possible to specifically detect each of the target genes and to detect the three kinds of genes. The detection by chromatography took as short a time as 10 to 15 minutes.

Example 10

(1) Synthesis of Artificial Nucleic Acid (Azobenzene)-Inserted Primer

In this example, *Escherichia coli* (*E. coli* DH5α) transfected with the plasmid pUC19 was used as a target. A forward primer (F) and a reverse primer (R) were designed to be able to amplify about 330 base pairs by PCR amplification using pUC19 as a template. Then, a polymerase reaction inhibitory region (X) containing azobenzene (artificial nucleic acid), and a tag sequence T37 or T38 were introduced into the 5' end of each corresponding primer to synthesize tagged primers T37-X-F and T38-X-R. These two azobenzene-inserted primers were purchased as products custom-synthesized by TSUKUBA OLIGO SERVICE CO., LTD. The following shows the primer set prepared in this study.

```
Tag sequence T37:
                                   (SEQ ID No: 103)
5'-Dd(TGGCAACATTTTTCACTGGGTTTATAG)-3'

Tag sequence T38:
                                   (SEQ ID No: 104)
5'-Dd(GGTTAGCTTCCAACCACGTGTAGATCA)-3'

Primer F:
                                   (SEQ ID No: 105)
5'-Dd(GGAAACAGCTATGACCATGA)-3'

Primer R:
                                   (SEQ ID No: 106)
5'-Dd(TCTATGCGGCATCAGAGCAG)-3'

Primer T37-X-F:
                                   (SEQ ID No: 107)
5'-Dd(TGGCAACATTTTTCACTGGGTTTATAG X
GGAAACAGCTATGACCATGA)-3'

Primer T38-X-R:
                                   (SEQ ID No: 108)
5'-Dd(GGTTAGCTTCCAACCACGTGTAGATCA X
TCTATGCGGCATCAGAGCAG)-3'
```

(2) PCR Using Azobenzene-Inserted Primer Set

A colony of *Escherichia coli* (*E. coli* DH5α) cells transfected with the plasmid pUC19 was collected and mixed in 1 ml of water. PCR was performed using the primer set prepared in the above step (1). Specifically, a 25 μl PCR mixture was prepared by putting the primer F and primer R (5 pmol each) and the *Escherichia coli* suspension (1 μl) in a 0.2-ml PCR tube, and following the instruction manual of a PCR device ExTaq (available from Takara Bio, Inc.). Subsequently, the tube was set in a thermal cycler (GeneAmp PCR System, available from Applied Biosystems), and subjected to heat treatment at 95° C. for five minutes and then exposed to 30 cycles of 95° C. for 30 seconds, 55° C. for 30 seconds, and 72° C. for 30 seconds. Consequently, the target fragment of about 330 bp was amplified. Separately, the same reaction was carried out in the absence of the suspension as a negative control.

(3) Preparation of Gold Colloid-Bound Oligonucleotide Probe

Gold Colloid (10 nm, $5.7 \times 10^{12}$ (particles/ml), available from British BioCell International) and an anti-FITC antibody solution (5 mM phosphate buffer, pH 7) were mixed and left to stand still for 20 minutes at room temperature. To the resulting mixture, one half volume of a solution of 1% BSA and 0.1% PEG was added, and the mixture was centrifuged at 10000 rpm for 25 minutes. After removing the supernatant, the residue was combined and mixed with the solution of 1% BSA and 0.1% PEG, and the mixture was then centrifuged at 10000 rpm for 25 minutes. After the centrifugation, the supernatant was removed and the residue was combined with 5 mM phosphate buffer (pH 7). This buffer replacement procedure was performed again.

The obtained gold colloid solution was mixed with a 3'-FITC-modified oligonucleotide probe 40 (SEQ ID No: 109, strand complementary to SEQ ID No: 103). The mixture was uniformly applied to a glass fiber pad, and the pad was then dried in a vacuum oven. In this manner, a conjugate pad was obtained.

```
Oligonucleotide probe 40:
                                     (SEQ ID No: 109)
  5'-Dd(CTATAAACCCAGTGAAAAATGTTGCCA)-FITC-3'
```

(4) Immobilization of Oligonucleotide Probe on Solid Phase

A 3'-biotin-modified oligonucleotide probe 41 having a sequence (SEQ ID No: 110) complementary to SEQ ID No: 104 was mixed with streptavidin. The resulting mixture was applied with a dispenser along a line on a nitrocellulose membrane (product name: Hi-Flow 180, available from Millipore Corporation), and air-dried at 40° C. for 30 minutes.

```
Oligonucleotide probe 41:
                                     (SEQ ID No: 110)
  5'-Dd(GATCATACACGTGGTTGGAAGCTAACC)-Biotin-3'
```

(5) Preparation of Nucleic Acid Chromatography-Like Test Strip

A test strip to be used for detection of the PCR product amplified using the azobenzene-inserted primer set was prepared by attaching a chromatographic medium consisting of the nitrocellulose membrane prepared above, the conjugate pad prepared above, a general sample pad as a sample application zone, and an absorption pad for absorbing the developed sample and the labeling substance to a substrate consisting of a backing sheet as shown in FIG. 6.

(6) Detection of PCR Product Using Test Strip

The PCR product obtained in the step (2) was immediately, without being denatured, applied to the sample application zone on the test strip prepared in the step (5) to perform detection by chromatography. A colored line specific to the target nucleic acid was detected along the test line for the sample prepared using *Escherichia coli* cells as an analyte in the step (2). In contrast, there was no line detected for the negative control prepared without using *Escherichia coli* cells. The detection by chromatography took as short a time as 10 to 15 minutes.

REFERENCE SIGNS LIST

1. Primer region
2. Tag region
3. Polymerase reaction inhibitory region (spacer region)
4. Primer region of first primer (joint primer)
5. Common sequence of first primer (joint primer)
6. Common sequence of second primer
7. Tag region of second primer
8. Polymerase reaction inhibitory region (spacer region) of second primer
9. Target nucleic acid sequence
10. Forward primer
11. Primer region of forward primer
12. Tag region of forward primer
13. Reverse primer
14. Primer region of reverse primer
15. Tag region of reverse primer
16. PCR product having a partially double-stranded nucleic acid structure
17. Target nucleic acid sequence
18. First forward primer
19. Primer region of first forward primer
20. Tag region of first forward primer
21. First reverse primer
22. Primer region of first reverse primer
23. Tag region of first reverse primer
24. Double-stranded PCR product synthesized with first primers
25. Second forward primer
26. Primer region of second forward primer
27. Tag region of second forward primer
28. Second reverse primer
29. Primer region of second reverse primer
30. Tag region of second reverse primer
31. PCR product having a partially double-stranded nucleic acid structure
32. Sample pad
33. Conjugate pad
34. Carrier having capture oligonucleotide
35. Absorption pad
36. Substrate
37. Test line
38. Control line
39. Oligonucleotide to be bonded to target molecule
40. Target molecule
41. PCR product-target molecule complex
42. Porous membrane
43. Capture oligonucleotide
44. Carrier (microarray) having capture oligonucleotide in each well
45. Bead carrier having capture oligonucleotide

The invention claimed is:

1. A nucleic acid detection method, comprising
performing a nucleic acid amplification reaction using two primers in the presence of a nucleic acid template and a DNA polymerase, thereby producing an amplified double-stranded DNA fragment consisting of two 5' single-stranded regions respectively located at its opposite ends, wherein each of the primers contains a space structure comprising a polymerase reaction inhibitory region located between 5' end and 3' end of each of the primers and the polymerase reaction inhibitory region inhibits a nucleic acid extension reaction catalyzed by a polymerase,
detecting the amplified double-stranded DNA fragment by following steps:
hybridizing a first oligonucleotide probe immobilized on a solid phase with one of the two 5' single-stranded regions of the amplified double-stranded DNA fragment,
hybridizing a second oligonucleotide probe labeled with a labeling substance with the other region of the two 5' single-stranded regions of the amplified double stranded DNA fragment, and
detecting the presence of the amplified double-stranded DNA fragment.

2. The nucleic acid detection method according to claim 1, wherein the labeling substance comprises a colored carrier that allows the amplified double-stranded DNA fragment to be visually detected.

3. The nucleic acid detection method according to claim 2, wherein said detecting the amplified double-stranded DNA fragment comprises applying the amplified double-stranded DNA fragment on a nucleic acid detection device and said detecting the presence of the amplified DNA fragment is performed on the nucleic acid detection device and the solid phase is on the nucleic acid detection device.

4. The nucleic acid detection method according to claim 2, wherein said detecting the amplified double-stranded DNA fragment further comprises diffusing the amplified double-stranded DNA fragment by chromatography such that the presence of the amplified double-stranded DNA fragment is detected by the chromatography.

5. The nucleic acid detection method according to claim 1, wherein said detecting the amplified double-stranded DNA fragment comprises applying the amplified double-stranded DNA fragment on a nucleic acid detection device, said detecting the presence of the amplified double-stranded DNA fragment is performed on the nucleic acid detection device and the solid phase is on the nucleic acid detection device.

6. The nucleic acid detection method according to claim 5, wherein said detecting the amplified double-stranded DNA fragment further comprises following steps (a) to (c):
(a) performing said applying the amplified double-stranded DNA fragment on a nucleic acid detection device by placing the amplified double-stranded DNA fragment in a zone on the solid phase of the nucleic acid detection device which is different from a zone where the first oligonucleotide probe is immobilized on the solid phase;

(b) diffusing the amplified double-stranded DNA fragment with a solvent on the device toward the zone where the first oligonucleotide probe is immobilized; and (c) performing said hybridizing a first oligonucleotide probe immobilized on a solid phase with one of the two 5' single-stranded regions of the amplified double-stranded DNA fragment by hybridizing the first oligonucleotide probe with the amplified double-stranded DNA fragment in the zone where the first oligonucleotide probe is immobilized.

7. The nucleic acid detection method according to claim 6, wherein said hybridizing the second oligonucleotide probe labeled with a labeling substance with the amplified double-stranded DNA fragment is performed before the step (c).

8. The nucleic acid detection method according to claim 5, wherein said detecting the amplified double-stranded DNA fragment further comprises following steps (a) to (e):

(a) performing said applying the amplified double-stranded DNA fragment on a nucleic acid detection device by placing the amplified double-stranded DNA fragment and the second oligonucleotide probe respectively in discrete zones on the solid phase of the nucleic acid detection device which are different from a zone where the first oligonucleotide probe is immobilized on the solid phase; then (b) diffusing the amplified double-stranded DNA fragment with a solvent toward the zone of said discrete zones where the second oligonucleotide probe is placed; then (c) performing said hybridizing a second oligonucleotide probe labeled with a labeling substance with the other region of the two 5' single-stranded regions of the amplified double stranded DNA fragment by hybridizing the second oligonucleotide probe with the amplified double-stranded DNA fragment in the zone of said discrete zones where the second oligonucleotide probe is placed, thereby forming a hybridization complex;

(d) diffusing the hybridization complex obtained in the step (c) on the solid phase toward the zone where the first oligonucleotide probe is immobilized; and (e) performing said hybridizing a first oligonucleotide probe immobilized on a solid phase with one of the two 5' single-stranded regions of the amplified double-stranded DNA fragment by hybridizing the first oligonucleotide probe with the amplified double-stranded DNA fragment in the hybridization complex in the zone where the first oligonucleotide probe is immobilized.

9. The nucleic acid detection method according to claim 5, wherein the nucleic acid detection device is a device comprising a chromatography and said detecting the amplified double-stranded DNA fragment further comprises diffusing the amplified double-stranded DNA fragment by the chromatography such that the presence of the amplified double-stranded DNA fragment is detected by the chromatography.

10. The nucleic acid detection method according to claim 1, wherein said detecting the amplified double-stranded DNA fragment further comprises diffusing the amplified double-stranded DNA fragment by chromatography such that the presence of the amplified double-stranded DNA fragment is detected by the chromatography.

11. The nucleic acid detection method according to claim 1, wherein each of the two 5' single-stranded regions of the amplified double-stranded DNA fragment has a 5' tag sequence from a 5' tag sequence of each of the primers.

12. The nucleic acid detection method according to claim 1, wherein the first primer of the two primers comprises a sequence capable of hybridizing to one strand of the nucleic acid template and a common sequence incapable of hybridizing to the template, and the second primer of the two primers comprises a sequence capable of hybridizing to other strand of the nucleic acid template and a tag region incapable of hybridizing to the template.

13. The nucleic acid detection method according to claim 12, wherein the tag region comprises natural nucleotides.

* * * * *

SEQUENCE LISTING

```
<160> NUMBER OF SEQ ID NOS: 110

<210> SEQ ID NO 1
<211> LENGTH: 20
<212> TYPE: DNA
<213> ORGANISM: Artificial
<220> FEATURE:
<223> OTHER INFORMATION: Primer F
```

-continued

<400> SEQUENCE: 1
ggaaacagct atgaccatga                                              20

<210> SEQ ID NO 2
<211> LENGTH: 19
<212> TYPE: DNA
<213> ORGANISM: Artificial
<220> FEATURE:
<223> OTHER INFORMATION: Primer R

<400> SEQUENCE: 2
ctatgcggca tcagagcag                                               19

<210> SEQ ID NO 3
<211> LENGTH: 20
<212> TYPE: DNA
<213> ORGANISM: Artificial
<220> FEATURE:
<223> OTHER INFORMATION: Tag sequence T1
<220> FEATURE:
<221> NAME/KEY: misc_feature
<222> LOCATION: (1)..(20)
<223> OTHER INFORMATION: L-form DNA

<400> SEQUENCE: 3
gacaacggag acagagccaa                                              20

<210> SEQ ID NO 4
<211> LENGTH: 20
<212> TYPE: DNA
<213> ORGANISM: Artificial
<220> FEATURE:
<223> OTHER INFORMATION: Tag sequence T2
<220> FEATURE:
<221> NAME/KEY: misc_feature
<222> LOCATION: (1)..(20)
<223> OTHER INFORMATION: L-form DNA

<400> SEQUENCE: 4
atgctaccgt atgcccagtg                                              20

<210> SEQ ID NO 5
<211> LENGTH: 40
<212> TYPE: DNA
<213> ORGANISM: Artificial
<220> FEATURE:
<223> OTHER INFORMATION: Primer T1-F
<220> FEATURE:
<221> NAME/KEY: misc_feature
<222> LOCATION: (1)..(20)
<223> OTHER INFORMATION: L-form DNA

<400> SEQUENCE: 5
gacaacggag acagagccaa ggaaacagct atgaccatga                        40

<210> SEQ ID NO 6
<211> LENGTH: 39
<212> TYPE: DNA
<213> ORGANISM: Artificial
<220> FEATURE:
<223> OTHER INFORMATION: Primer T2-R
<220> FEATURE:
<221> NAME/KEY: misc_feature
<222> LOCATION: (1)..(20)
<223> OTHER INFORMATION: L-form DNA

<400> SEQUENCE: 6
atgctaccgt atgcccagtg ctatgcggca tcagagcag                    39

<210> SEQ ID NO 7
<211> LENGTH: 20
<212> TYPE: DNA
<213> ORGANISM: Artificial
<220> FEATURE:
<223> OTHER INFORMATION: Probe 1
<220> FEATURE:
<221> NAME/KEY: misc_feature
<222> LOCATION: (1)..(20)
<223> OTHER INFORMATION: L-form DNA
<220> FEATURE:
<221> NAME/KEY: modified_base
<222> LOCATION: (20)..(20)
<223> OTHER INFORMATION: modified with amino group.

<400> SEQUENCE: 7
ttggctctgt ctccgttgtc                                         20

<210> SEQ ID NO 8
<211> LENGTH: 20
<212> TYPE: DNA
<213> ORGANISM: Artificial
<220> FEATURE:
<223> OTHER INFORMATION: Probe 2
<220> FEATURE:
<221> NAME/KEY: misc_feature
<222> LOCATION: (1)..(20)
<223> OTHER INFORMATION: L-form DNA
<220> FEATURE:
<221> NAME/KEY: modified_base
<222> LOCATION: (20)..(20)
<223> OTHER INFORMATION: modified with amino group.

<400> SEQUENCE: 8
cactgggcat acggtagcat                                         20

<210> SEQ ID NO 9
<211> LENGTH: 42
<212> TYPE: DNA
<213> ORGANISM: Artificial
<220> FEATURE:
<223> OTHER INFORMATION: PCR inhibitory sequence H

<400> SEQUENCE: 9
aggcgaggtc gcgagcgcac atgtgcgctc gcgacctcgc ct                42

<210> SEQ ID NO 10
<211> LENGTH: 25
<212> TYPE: DNA
<213> ORGANISM: Artificial
<220> FEATURE:
<223> OTHER INFORMATION: Tag sequence T3

<400> SEQUENCE: 10
tatgatatgc ttctccacgc ataat                                   25

<210> SEQ ID NO 11
<211> LENGTH: 21
<212> TYPE: DNA
<213> ORGANISM: Artificial
<220> FEATURE:
<223> OTHER INFORMATION: Tag sequence T4

<400> SEQUENCE: 11
tgctctgtac acttgctcaa t                                       21

```
<210> SEQ ID NO 12
<211> LENGTH: 87
<212> TYPE: DNA
<213> ORGANISM: Artificial
<220> FEATURE:
<223> OTHER INFORMATION: Primer T3-H-F

<400> SEQUENCE: 12
tatgatatgc ttctccacgc ataataggcg aggtcgcgag cgcacatgtg cgctcgcgac    60
ctcgcctgga aacagctatg accatga                                       87

<210> SEQ ID NO 13
<211> LENGTH: 82
<212> TYPE: DNA
<213> ORGANISM: Artificial
<220> FEATURE:
<223> OTHER INFORMATION: Primer T4-H-R

<400> SEQUENCE: 13
tgctctgtac acttgctcaa taggcgaggt cgcgagcgca catgtgcgct cgcgacctcg    60
cctctatgcg gcatcagagc ag                                            82

<210> SEQ ID NO 14
<211> LENGTH: 25
<212> TYPE: DNA
<213> ORGANISM: Artificial
<220> FEATURE:
<223> OTHER INFORMATION: Probe 3
<220> FEATURE:
<221> NAME/KEY: modified_base
<222> LOCATION: (25)..(25)
<223> OTHER INFORMATION: modified with amino group.

<400> SEQUENCE: 14
attatgcgtg gagaagcata tcata                                         25

<210> SEQ ID NO 15
<211> LENGTH: 21
<212> TYPE: DNA
<213> ORGANISM: Artificial
<220> FEATURE:
<223> OTHER INFORMATION: Probe 4
<220> FEATURE:
<221> NAME/KEY: modified_base
<222> LOCATION: (21)..(21)
<223> OTHER INFORMATION: modified with amino group.

<400> SEQUENCE: 15
attgagcaag tgtacagagc a                                             21

<210> SEQ ID NO 16
<211> LENGTH: 27
<212> TYPE: DNA
<213> ORGANISM: Artificial
<220> FEATURE:
<223> OTHER INFORMATION: Tag sequence T5

<400> SEQUENCE: 16
tggcaacatt tttcactggg tttatag                                       27

<210> SEQ ID NO 17
<211> LENGTH: 27
<212> TYPE: DNA
<213> ORGANISM: Artificial
<220> FEATURE:
<223> OTHER INFORMATION: Tag sequence T6
```

<400> SEQUENCE: 17
ggttagcttc caaccacgtg tagatca                                              27

<210> SEQ ID NO 18
<211> LENGTH: 47
<212> TYPE: DNA
<213> ORGANISM: Artificial
<220> FEATURE:
<223> OTHER INFORMATION: Primer T5-X-F
<220> FEATURE:
<221> NAME/KEY: misc_feature
<222> LOCATION: (27)..(28)
<223> OTHER INFORMATION: g at position 27 is jointed to g at position 28
      by azobenzene represented by Formula (1) of the specification.

<400> SEQUENCE: 18
tggcaacatt tttcactggg tttataggga aacagctatg accatga                        47

<210> SEQ ID NO 19
<211> LENGTH: 47
<212> TYPE: DNA
<213> ORGANISM: Artificial
<220> FEATURE:
<223> OTHER INFORMATION: Primer T6-X-R
<220> FEATURE:
<221> NAME/KEY: misc_feature
<222> LOCATION: (27)..(28)
<223> OTHER INFORMATION: a at position 27 is jointed to t at position 28 by azobenzene
      represented by Formula (1) of the specification.

<400> SEQUENCE: 19
ggttagcttc caaccacgtg tagatcatct atgcggcatc agagcag                        47

<210> SEQ ID NO 20
<211> LENGTH: 27
<212> TYPE: DNA
<213> ORGANISM: Artificial
<220> FEATURE:
<223> OTHER INFORMATION: Probe 5
<220> FEATURE:
<221> NAME/KEY: modified_base
<222> LOCATION: (27)..(27)
<223> OTHER INFORMATION: modified with amino group.

<400> SEQUENCE: 20
ctataaaccc agtgaaaaat gttgcca                                              27

<210> SEQ ID NO 21
<211> LENGTH: 27
<212> TYPE: DNA
<213> ORGANISM: Artificial
<220> FEATURE:
<223> OTHER INFORMATION: Probe 6
<220> FEATURE:
<221> NAME/KEY: modified_base
<222> LOCATION: (27)..(27)
<223> OTHER INFORMATION: modified with amino group.

<400> SEQUENCE: 21
gatcatacac gtggttggaa gctaacc                                              27

<210> SEQ ID NO 22
<211> LENGTH: 27
<212> TYPE: DNA
<213> ORGANISM: Artificial
<220> FEATURE:
<223> OTHER INFORMATION: Probe 7
<220> FEATURE:
<221> NAME/KEY: modified_base

```
<222> LOCATION: (27)..(27)
<223> OTHER INFORMATION: modified with thiol group.

<400> SEQUENCE: 22
ctataaaccc agtgaaaaat gttgcca                                          27

<210> SEQ ID NO 23
<211> LENGTH: 27
<212> TYPE: DNA
<213> ORGANISM: Artificial
<220> FEATURE:
<223> OTHER INFORMATION: Probe 8
<220> FEATURE:
<221> NAME/KEY: modified_base
<222> LOCATION: (20)..(20)
<223> OTHER INFORMATION: modified with biotin.

<400> SEQUENCE: 23
gatcatacac gtggttggaa gctaacc                                          27

<210> SEQ ID NO 24
<211> LENGTH: 27
<212> TYPE: DNA
<213> ORGANISM: Artificial
<220> FEATURE:
<223> OTHER INFORMATION: Probe 9

<400> SEQUENCE: 24
gatcatacac gtggttggaa gctaacc                                          27

<210> SEQ ID NO 25
<211> LENGTH: 27
<212> TYPE: DNA
<213> ORGANISM: Artificial
<220> FEATURE:
<223> OTHER INFORMATION: Tag sequence T10

<400> SEQUENCE: 25
tggcaacatt tttcactggg tttatag                                          27

<210> SEQ ID NO 26
<211> LENGTH: 27
<212> TYPE: DNA
<213> ORGANISM: Artificial
<220> FEATURE:
<223> OTHER INFORMATION: Tag sequence T11

<400> SEQUENCE: 26
ggttagcttc caaccacgtg tagatca                                          27

<210> SEQ ID NO 27
<211> LENGTH: 47
<212> TYPE: DNA
<213> ORGANISM: Artificial
<220> FEATURE:
<223> OTHER INFORMATION: Primer T10-X-F1
<220> FEATURE:
<221> NAME/KEY: misc_feature
<222> LOCATION: (27)..(28)
<223> OTHER INFORMATION: g at position 27 is jointed to g at position 28
      by azobenzene represented by Formula (1) of the specification.

<400> SEQUENCE: 27
tggcaacatt tttcactggg tttataggga aacagctatg accatga                    47

<210> SEQ ID NO 28
<211> LENGTH: 47
```

```
<212> TYPE: DNA
<213> ORGANISM: Artificial
<220> FEATURE:
<223> OTHER INFORMATION: Primer T11-X-R1
<220> FEATURE:
<221> NAME/KEY: misc_feature
<222> LOCATION: (27)..(28)
<223> OTHER INFORMATION: a at position 27 is jointed to t at position 28
      by azobenzene represented by Formula (1) of the specification.

<400> SEQUENCE: 28
ggttagcttc caaccacgtg tagatcatct atgcggcatc agagcag                    47

<210> SEQ ID NO 29
<211> LENGTH: 25
<212> TYPE: DNA
<213> ORGANISM: Artificial
<220> FEATURE:
<223> OTHER INFORMATION: Tag sequence T12

<400> SEQUENCE: 29
cgcattgagc aagtgtacag agcat                                            25

<210> SEQ ID NO 30
<211> LENGTH: 25
<212> TYPE: DNA
<213> ORGANISM: Artificial
<220> FEATURE:
<223> OTHER INFORMATION: Tag sequence T13

<400> SEQUENCE: 30
attatgcgtg gagaagcata tcata                                            25

<210> SEQ ID NO 31
<211> LENGTH: 45
<212> TYPE: DNA
<213> ORGANISM: Artificial
<220> FEATURE:
<223> OTHER INFORMATION: Primer T12-X-F2
<220> FEATURE:
<221> NAME/KEY: misc_feature
<222> LOCATION: (25)..(26)
<223> OTHER INFORMATION: t at position 25 is jointed to a at position 26
      by azobenzene represented by Formula (1) of the specification.

<400> SEQUENCE: 31
cgcattgagc aagtgtacag agcatagcat tatgaattat atggt                      45

<210> SEQ ID NO 32
<211> LENGTH: 45
<212> TYPE: DNA
<213> ORGANISM: Artificial
<220> FEATURE:
<223> OTHER INFORMATION: Primer T13-X-R2
<220> FEATURE:
<221> NAME/KEY: misc_feature
<222> LOCATION: (25)..(26)
<223> OTHER INFORMATION: a at position 25 is jointed to t at position 26
      by azobenzene represented by Formula (1) of the specification.

<400> SEQUENCE: 32
attatgcgtg gagaagcata tcatattgtt tacatttata gcatc                      45

<210> SEQ ID NO 33
<211> LENGTH: 22
<212> TYPE: DNA
<213> ORGANISM: Artificial
<220> FEATURE:
<223> OTHER INFORMATION: Tag sequence T14
```

```
<400> SEQUENCE: 33
aattgcgcat gtccatgtgt aa                                              22

<210> SEQ ID NO 34
<211> LENGTH: 22
<212> TYPE: DNA
<213> ORGANISM: Artificial
<220> FEATURE:
<223> OTHER INFORMATION: Tag sequence T15

<400> SEQUENCE: 34
tactttagag gaaactgctg ag                                              22

<210> SEQ ID NO 35
<211> LENGTH: 42
<212> TYPE: DNA
<213> ORGANISM: Artificial
<220> FEATURE:
<223> OTHER INFORMATION: Primer T14-X-F3
<220> FEATURE:
<221> NAME/KEY: misc_feature
<222> LOCATION: (22)..(23)
<223> OTHER INFORMATION: a at position 22 is jointed to t at position 23
      by azobenzene represented by Formula (1) of the specification.

<400> SEQUENCE: 35
aattgcgcat gtccatgtgt aatggtttta aaactctgat ac                        42

<210> SEQ ID NO 36
<211> LENGTH: 42
<212> TYPE: DNA
<213> ORGANISM: Artificial
<220> FEATURE:
<223> OTHER INFORMATION: Primer T15-X-R3
<220> FEATURE:
<221> NAME/KEY: misc_feature
<222> LOCATION: (22)..(23)
<223> OTHER INFORMATION: g at position 22 is jointed to a at position 23
      by azobenzene represented by Formula (1) of the specification.

<400> SEQUENCE: 36
tactttagag gaaactgctg agagtatgat gagggtgtaa ca                        42

<210> SEQ ID NO 37
<211> LENGTH: 27
<212> TYPE: DNA
<213> ORGANISM: Artificial
<220> FEATURE:
<223> OTHER INFORMATION: Probe 16
<220> FEATURE:
<221> NAME/KEY: modified_base
<222> LOCATION: (27)..(27)
<223> OTHER INFORMATION: modified with amino group.

<400> SEQUENCE: 37
ctataaaccc agtgaaaaat gttgcca                                         27

<210> SEQ ID NO 38
<211> LENGTH: 25
<212> TYPE: DNA
<213> ORGANISM: Artificial
<220> FEATURE:
<223> OTHER INFORMATION: Probe 17
<220> FEATURE:
<221> NAME/KEY: modified_base
<222> LOCATION: (25)..(25)
<223> OTHER INFORMATION: modified with amino group.
```

```
<400> SEQUENCE: 38
ttgctctgta cacttgctca atgcg                                              25

<210> SEQ ID NO 39
<211> LENGTH: 22
<212> TYPE: DNA
<213> ORGANISM: Artificial
<220> FEATURE:
<223> OTHER INFORMATION: Probe 18
<220> FEATURE:
<221> NAME/KEY: modified_base
<222> LOCATION: (22)..(22)
<223> OTHER INFORMATION: modified with amino group.

<400> SEQUENCE: 39
ttacacatgg acatgcgcaa tt                                                 22

<210> SEQ ID NO 40
<211> LENGTH: 27
<212> TYPE: DNA
<213> ORGANISM: Artificial
<220> FEATURE:
<223> OTHER INFORMATION: Probe 19
<220> FEATURE:
<221> NAME/KEY: modified_base
<222> LOCATION: (27)..(27)
<223> OTHER INFORMATION: modified with biotin.

<400> SEQUENCE: 40
gatcatacac gtggttggaa gctaacc                                            27

<210> SEQ ID NO 41
<211> LENGTH: 25
<212> TYPE: DNA
<213> ORGANISM: Artificial
<220> FEATURE:
<223> OTHER INFORMATION: Probe 20
<220> FEATURE:
<221> NAME/KEY: modified_base
<222> LOCATION: (25)..(25)
<223> OTHER INFORMATION: modified with biotin.

<400> SEQUENCE: 41
tatgatatgc ttctccacgc ataat                                              25

<210> SEQ ID NO 42
<211> LENGTH: 22
<212> TYPE: DNA
<213> ORGANISM: Artificial
<220> FEATURE:
<223> OTHER INFORMATION: Probe 21
<220> FEATURE:
<221> NAME/KEY: modified_base
<222> LOCATION: (22)..(22)
<223> OTHER INFORMATION: modified with biotin.

<400> SEQUENCE: 42
ctcagcagtt tcctctaaag ta                                                 22

<210> SEQ ID NO 43
<211> LENGTH: 20
<212> TYPE: DNA
<213> ORGANISM: Artificial
<220> FEATURE:
<223> OTHER INFORMATION: Common sequence KF1

<400> SEQUENCE: 43
tgggctgacc tagaggtctt                                                    20
```

<210> SEQ ID NO 44
<211> LENGTH: 20
<212> TYPE: DNA
<213> ORGANISM: Artificial
<220> FEATURE:
<223> OTHER INFORMATION: Common sequence KR1

<400> SEQUENCE: 44
atgaaatgca ggccattcgg                                                    20

<210> SEQ ID NO 45
<211> LENGTH: 40
<212> TYPE: DNA
<213> ORGANISM: Artificial
<220> FEATURE:
<223> OTHER INFORMATION: Primer KF1-Fj1

<400> SEQUENCE: 45
tgggctgacc tagaggtctt ggaaacagct atgaccatga                              40

<210> SEQ ID NO 46
<211> LENGTH: 40
<212> TYPE: DNA
<213> ORGANISM: Artificial
<220> FEATURE:
<223> OTHER INFORMATION: Primer KR1-Rj1

<400> SEQUENCE: 46
atgaaatgca ggccattcgg tctatgcggc atcagagcag                              40

<210> SEQ ID NO 47
<211> LENGTH: 20
<212> TYPE: DNA
<213> ORGANISM: Artificial
<220> FEATURE:
<223> OTHER INFORMATION: Common sequence KF2

<400> SEQUENCE: 47
ccggaacaga caccaggttt                                                    20

<210> SEQ ID NO 48
<211> LENGTH: 20
<212> TYPE: DNA
<213> ORGANISM: Artificial
<220> FEATURE:
<223> OTHER INFORMATION: Common sequence KR2

<400> SEQUENCE: 48
gaagctgtac cgtcacatga                                                    20

<210> SEQ ID NO 49
<211> LENGTH: 40
<212> TYPE: DNA
<213> ORGANISM: Artificial
<220> FEATURE:
<223> OTHER INFORMATION: Primer KF2-Fj2

<400> SEQUENCE: 49
ccggaacaga caccaggttt agcattatga attatatggt                              40

<210> SEQ ID NO 50
<211> LENGTH: 40
<212> TYPE: DNA
<213> ORGANISM: Artificial
<220> FEATURE:

<223> OTHER INFORMATION: Primer KR2-Rj2

<400> SEQUENCE: 50
gaagctgtac cgtcacatga ttgtttacat ttatagcatc            40

<210> SEQ ID NO 51
<211> LENGTH: 20
<212> TYPE: DNA
<213> ORGANISM: Artificial
<220> FEATURE:
<223> OTHER INFORMATION: Common sequence KF3

<400> SEQUENCE: 51
ataccgatga gtgtgctacc            20

<210> SEQ ID NO 52
<211> LENGTH: 20
<212> TYPE: DNA
<213> ORGANISM: Artificial
<220> FEATURE:
<223> OTHER INFORMATION: Common sequence KR3

<400> SEQUENCE: 52
tggcctgtgt gacactatgc            20

<210> SEQ ID NO 53
<211> LENGTH: 40
<212> TYPE: DNA
<213> ORGANISM: Artificial
<220> FEATURE:
<223> OTHER INFORMATION: Primer KF3-Fj3

<400> SEQUENCE: 53
ataccgatga gtgtgctacc tggttttaaa actctgatac            40

<210> SEQ ID NO 54
<211> LENGTH: 40
<212> TYPE: DNA
<213> ORGANISM: Artificial
<220> FEATURE:
<223> OTHER INFORMATION: Primer KR3-Rj3

<400> SEQUENCE: 54
tggcctgtgt gacactatgc agtatgatga gggtgtaaca            40

<210> SEQ ID NO 55
<211> LENGTH: 27
<212> TYPE: DNA
<213> ORGANISM: Artificial
<220> FEATURE:
<223> OTHER INFORMATION: Tag sequence T22

<400> SEQUENCE: 55
tggcaacatt tttcactggg tttatag            27

<210> SEQ ID NO 56
<211> LENGTH: 27
<212> TYPE: DNA
<213> ORGANISM: Artificial
<220> FEATURE:
<223> OTHER INFORMATION: Tag sequence T23

<400> SEQUENCE: 56
ggttagcttc caaccacgtg tagatca            27

```
<210> SEQ ID NO 57
<211> LENGTH: 47
<212> TYPE: DNA
<213> ORGANISM: Artificial
<220> FEATURE:
<223> OTHER INFORMATION: Primer T22-X-KF1
<220> FEATURE:
<221> NAME/KEY: misc_feature
<222> LOCATION: (27)..(28)
<223> OTHER INFORMATION: g at position 27 is jointed to t at position 28
      by azobenzene represented by Formula (1) of the specification.

<400> SEQUENCE: 57
tggcaacatt tttcactggg tttatagtgg gctgacctag aggtctt                    47

<210> SEQ ID NO 58
<211> LENGTH: 47
<212> TYPE: DNA
<213> ORGANISM: Artificial
<220> FEATURE:
<223> OTHER INFORMATION: Primer T23-X-KR1
<220> FEATURE:
<221> NAME/KEY: misc_feature
<222> LOCATION: (27)..(28)
<223> OTHER INFORMATION: a at position 27 is jointed to a at position 28
      by azobenzene represented by Formula (1) of the specification.

<400> SEQUENCE: 58
ggttagcttc caaccacgtg tagatcaatg aaatgcaggc cattcgg                    47

<210> SEQ ID NO 59
<211> LENGTH: 25
<212> TYPE: DNA
<213> ORGANISM: Artificial
<220> FEATURE:
<223> OTHER INFORMATION: Tag sequence T24

<400> SEQUENCE: 59
cgcattgagc aagtgtacag agcat                                            25

<210> SEQ ID NO 60
<211> LENGTH: 25
<212> TYPE: DNA
<213> ORGANISM: Artificial
<220> FEATURE:
<223> OTHER INFORMATION: Tag sequence T25

<400> SEQUENCE: 60
attatgcgtg gagaagcata tcata                                            25

<210> SEQ ID NO 61
<211> LENGTH: 45
<212> TYPE: DNA
<213> ORGANISM: Artificial
<220> FEATURE:
<223> OTHER INFORMATION: Primer T24-X-KF2
<220> FEATURE:
<221> NAME/KEY: misc_feature
<222> LOCATION: (25)..(26)
<223> OTHER INFORMATION: t at position 25 is jointed to c at position 26
      by azobenzene represented by Formula (1) of the specification.

<400> SEQUENCE: 61
cgcattgagc aagtgtacag agcatccgga acagacacca ggttt                      45

<210> SEQ ID NO 62
<211> LENGTH: 45
<212> TYPE: DNA
<213> ORGANISM: Artificial
```

```
<220> FEATURE:
<223> OTHER INFORMATION: Primer T25-X-KR2
<220> FEATURE:
<221> NAME/KEY: misc_feature
<222> LOCATION: (25)..(26)
<223> OTHER INFORMATION: a at position 25 is jointed to g at position 26
      by azobenzene represented by Formula (1) of the specification.

<400> SEQUENCE: 62
attatgcgtg gagaagcata tcatagaagc tgtaccgtca catga              45

<210> SEQ ID NO 63
<211> LENGTH: 22
<212> TYPE: DNA
<213> ORGANISM: Artificial
<220> FEATURE:
<223> OTHER INFORMATION: Tag sequence T26

<400> SEQUENCE: 63
aattgcgcat gtccatgtgt aa                                        22

<210> SEQ ID NO 64
<211> LENGTH: 22
<212> TYPE: DNA
<213> ORGANISM: Artificial
<220> FEATURE:
<223> OTHER INFORMATION: Tag sequence T27

<400> SEQUENCE: 64
tactttagag gaaactgctg ag                                        22

<210> SEQ ID NO 65
<211> LENGTH: 42
<212> TYPE: DNA
<213> ORGANISM: Artificial
<220> FEATURE:
<223> OTHER INFORMATION: Primer T26-X-KF3
<220> FEATURE:
<221> NAME/KEY: misc_feature
<222> LOCATION: (22)..(23)
<223> OTHER INFORMATION: a at position 22 is jointed to a at position 23
      by azobenzene represented by Formula (1) of the specification.

<400> SEQUENCE: 65
aattgcgcat gtccatgtgt aaataccgat gagtgtgcta cc                  42

<210> SEQ ID NO 66
<211> LENGTH: 42
<212> TYPE: DNA
<213> ORGANISM: Artificial
<220> FEATURE:
<223> OTHER INFORMATION: Primer T27-X-KR3
<220> FEATURE:
<221> NAME/KEY: misc_feature
<222> LOCATION: (22)..(23)
<223> OTHER INFORMATION: g at position 22 is jointed to t at position 23
      by azobenzene represented by Formula (1) of the specification.

<400> SEQUENCE: 66
tactttagag gaaactgctg agtggcctgt gtgacactat gc                  42

<210> SEQ ID NO 67
<211> LENGTH: 27
<212> TYPE: DNA
<213> ORGANISM: Artificial
<220> FEATURE:
<223> OTHER INFORMATION: Probe 28
<220> FEATURE:
<221> NAME/KEY: modified_base
```

```
<222> LOCATION: (27)..(27)
<223> OTHER INFORMATION: modified with amino group.

<400> SEQUENCE: 67
ctataaaccc agtgaaaaat gttgcca                                              27

<210> SEQ ID NO 68
<211> LENGTH: 25
<212> TYPE: DNA
<213> ORGANISM: Artificial
<220> FEATURE:
<223> OTHER INFORMATION: Probe 29
<220> FEATURE:
<221> NAME/KEY: modified_base
<222> LOCATION: (25)..(25)
<223> OTHER INFORMATION: modified with amino group.

<400> SEQUENCE: 68
ttgctctgta cacttgctca atgcg                                                25

<210> SEQ ID NO 69
<211> LENGTH: 22
<212> TYPE: DNA
<213> ORGANISM: Artificial
<220> FEATURE:
<223> OTHER INFORMATION: Probe 30
<220> FEATURE:
<221> NAME/KEY: modified_base
<222> LOCATION: (22)..(22)
<223> OTHER INFORMATION: modified with amino group.

<400> SEQUENCE: 69
ttacacatgg acatgcgcaa tt                                                   22

<210> SEQ ID NO 70
<211> LENGTH: 27
<212> TYPE: DNA
<213> ORGANISM: Artificial
<220> FEATURE:
<223> OTHER INFORMATION: Probe 31
<220> FEATURE:
<221> NAME/KEY: modified_base
<222> LOCATION: (27)..(27)
<223> OTHER INFORMATION: modified with biotin.

<400> SEQUENCE: 70
gatcatacac gtggttggaa gctaacc                                              27

<210> SEQ ID NO 71
<211> LENGTH: 25
<212> TYPE: DNA
<213> ORGANISM: Artificial
<220> FEATURE:
<223> OTHER INFORMATION: Probe 32
<220> FEATURE:
<221> NAME/KEY: modified_base
<222> LOCATION: (25)..(25)
<223> OTHER INFORMATION: modified with biotin.

<400> SEQUENCE: 71
tatgatatgc ttctccacgc ataat                                                25

<210> SEQ ID NO 72
<211> LENGTH: 22
<212> TYPE: DNA
<213> ORGANISM: Artificial
<220> FEATURE:
<223> OTHER INFORMATION: Probe 33
<220> FEATURE:
```

```
<221> NAME/KEY: modified_base
<222> LOCATION: (22)..(22)
<223> OTHER INFORMATION: modified with biotin.

<400> SEQUENCE: 72
ctcagcagtt tcctctaaag ta                                                  22

<210> SEQ ID NO 73
<211> LENGTH: 20
<212> TYPE: DNA
<213> ORGANISM: Artificial
<220> FEATURE:
<223> OTHER INFORMATION: Common sequence KF

<400> SEQUENCE: 73
tgggctgacc tagaggtctt                                                     20

<210> SEQ ID NO 74
<211> LENGTH: 20
<212> TYPE: DNA
<213> ORGANISM: Artificial
<220> FEATURE:
<223> OTHER INFORMATION: Common sequence KR

<400> SEQUENCE: 74
atgaaatgca ggccattcgg                                                     20

<210> SEQ ID NO 75
<211> LENGTH: 40
<212> TYPE: DNA
<213> ORGANISM: Artificial
<220> FEATURE:
<223> OTHER INFORMATION: Primer KF-F

<400> SEQUENCE: 75
tgggctgacc tagaggtctt ggaaacagct atgaccatga                               40

<210> SEQ ID NO 76
<211> LENGTH: 40
<212> TYPE: DNA
<213> ORGANISM: Artificial
<220> FEATURE:
<223> OTHER INFORMATION: Primer KR-R

<400> SEQUENCE: 76
atgaaatgca ggccattcgg tctatgcggc atcagagcag                               40

<210> SEQ ID NO 77
<211> LENGTH: 20
<212> TYPE: DNA
<213> ORGANISM: Artificial
<220> FEATURE:
<223> OTHER INFORMATION: Primer KF2
<220> FEATURE:
<221> NAME/KEY: modified_base
<222> LOCATION: (1)..(1)
<223> OTHER INFORMATION: modified with biotin.

<400> SEQUENCE: 77
tgggctgacc tagaggtctt                                                     20

<210> SEQ ID NO 78
<211> LENGTH: 20
<212> TYPE: DNA
<213> ORGANISM: Artificial
<220> FEATURE:
<223> OTHER INFORMATION: Primer KR2
```

```
<220> FEATURE:
<221> NAME/KEY: modified_base
<222> LOCATION: (1)..(1)
<223> OTHER INFORMATION: modified with FITC.

<400> SEQUENCE: 78
atgaaatgca ggccattcgg                                               20

<210> SEQ ID NO 79
<211> LENGTH: 20
<212> TYPE: DNA
<213> ORGANISM: Artificial
<220> FEATURE:
<223> OTHER INFORMATION: Common sequence KF1

<400> SEQUENCE: 79
tgggctgacc tagaggtctt                                               20

<210> SEQ ID NO 80
<211> LENGTH: 20
<212> TYPE: DNA
<213> ORGANISM: Artificial
<220> FEATURE:
<223> OTHER INFORMATION: Common sequence KR1

<400> SEQUENCE: 80
atgaaatgca ggccattcgg                                               20

<210> SEQ ID NO 81
<211> LENGTH: 40
<212> TYPE: DNA
<213> ORGANISM: Artificial
<220> FEATURE:
<223> OTHER INFORMATION: Primer KF1-Fj1

<400> SEQUENCE: 81
tgggctgacc tagaggtctt ggaaacagct atgaccatga                         40

<210> SEQ ID NO 82
<211> LENGTH: 40
<212> TYPE: DNA
<213> ORGANISM: Artificial
<220> FEATURE:
<223> OTHER INFORMATION: Primer KR1-Rj1

<400> SEQUENCE: 82
atgaaatgca ggccattcgg tctatgcggc atcagagcag                         40

<210> SEQ ID NO 83
<211> LENGTH: 20
<212> TYPE: DNA
<213> ORGANISM: Artificial
<220> FEATURE:
<223> OTHER INFORMATION: Common sequence KF2

<400> SEQUENCE: 83
ccggaacaga caccaggttt                                               20

<210> SEQ ID NO 84
<211> LENGTH: 20
<212> TYPE: DNA
<213> ORGANISM: Artificial
<220> FEATURE:
<223> OTHER INFORMATION: Common sequence KR2

<400> SEQUENCE: 84
```
gaagctgtac cgtcacatga								20

<210> SEQ ID NO 85
<211> LENGTH: 40
<212> TYPE: DNA
<213> ORGANISM: Artificial
<220> FEATURE:
<223> OTHER INFORMATION: Primer KF2-Fj2

<400> SEQUENCE: 85
ccggaacaga caccaggttt agcattatga attatatggt								40

<210> SEQ ID NO 86
<211> LENGTH: 40
<212> TYPE: DNA
<213> ORGANISM: Artificial
<220> FEATURE:
<223> OTHER INFORMATION: Primer KR2-Rj2

<400> SEQUENCE: 86
gaagctgtac cgtcacatga ttgtttacat ttatagcatc								40

<210> SEQ ID NO 87
<211> LENGTH: 20
<212> TYPE: DNA
<213> ORGANISM: Artificial
<220> FEATURE:
<223> OTHER INFORMATION: Common sequence KF3

<400> SEQUENCE: 87
ataccgatga gtgtgctacc								20

<210> SEQ ID NO 88
<211> LENGTH: 20
<212> TYPE: DNA
<213> ORGANISM: Artificial
<220> FEATURE:
<223> OTHER INFORMATION: Common sequence KR3

<400> SEQUENCE: 88
tggcctgtgt gacactatgc								20

<210> SEQ ID NO 89
<211> LENGTH: 40
<212> TYPE: DNA
<213> ORGANISM: Artificial
<220> FEATURE:
<223> OTHER INFORMATION: Primer KF3-Fj3

<400> SEQUENCE: 89
ataccgatga gtgtgctacc tggttttaaa actctgatac								40

<210> SEQ ID NO 90
<211> LENGTH: 40
<212> TYPE: DNA
<213> ORGANISM: Artificial
<220> FEATURE:
<223> OTHER INFORMATION: Primer KR3-Rj3

<400> SEQUENCE: 90
tggcctgtgt gacactatgc agtatgatga gggtgtaaca								40

<210> SEQ ID NO 91
<211> LENGTH: 27
<212> TYPE: DNA
<213> ORGANISM: Artificial

```
<220> FEATURE:
<223> OTHER INFORMATION: Tag sequence T34

<400> SEQUENCE: 91
ggttagcttc caaccacgtg tagatca                                          27

<210> SEQ ID NO 92
<211> LENGTH: 20
<212> TYPE: DNA
<213> ORGANISM: Artificial
<220> FEATURE:
<223> OTHER INFORMATION: Primer KF1
<220> FEATURE:
<221> NAME/KEY: modified_base
<222> LOCATION: (1)..(1)
<223> OTHER INFORMATION: modified with biotin.

<400> SEQUENCE: 92
tgggctgacc tagaggtctt                                                  20

<210> SEQ ID NO 93
<211> LENGTH: 47
<212> TYPE: DNA
<213> ORGANISM: Artificial
<220> FEATURE:
<223> OTHER INFORMATION: Primer T34-X-KR1
<220> FEATURE:
<221> NAME/KEY: misc_feature
<222> LOCATION: (27)..(28)
<223> OTHER INFORMATION: a at position 27 is jointed to a at position 28
      by azobenzene represented by Formula (1) of the specification.

<400> SEQUENCE: 93
ggttagcttc caaccacgtg tagatcaatg aaatgcaggc cattcgg                    47

<210> SEQ ID NO 94
<211> LENGTH: 25
<212> TYPE: DNA
<213> ORGANISM: Artificial
<220> FEATURE:
<223> OTHER INFORMATION: Tag sequence T35

<400> SEQUENCE: 94
attatgcgtg gagaagcata tcata                                            25

<210> SEQ ID NO 95
<211> LENGTH: 20
<212> TYPE: DNA
<213> ORGANISM: Artificial
<220> FEATURE:
<223> OTHER INFORMATION: Primer KF2
<220> FEATURE:
<221> NAME/KEY: modified_base
<222> LOCATION: (1)..(1)
<223> OTHER INFORMATION: modified with biotin.

<400> SEQUENCE: 95
ccggaacaga caccaggttt                                                  20

<210> SEQ ID NO 96
<211> LENGTH: 45
<212> TYPE: DNA
<213> ORGANISM: Artificial
<220> FEATURE:
<223> OTHER INFORMATION: Primer T35-X-KR2
<220> FEATURE:
<221> NAME/KEY: misc_feature
<222> LOCATION: (25)..(26)
<223> OTHER INFORMATION: a at position 25 is jointed to g at position 26
``` by azobenzene represented by Formula (1) of the specification.

<400> SEQUENCE: 96
attatgcgtg gagaagcata tcatagaagc tgtaccgtca catga                45

<210> SEQ ID NO 97
<211> LENGTH: 22
<212> TYPE: DNA
<213> ORGANISM: Artificial
<220> FEATURE:
<223> OTHER INFORMATION: Tag sequence T36

<400> SEQUENCE: 97
tactttagag gaaactgctg ag                                         22

<210> SEQ ID NO 98
<211> LENGTH: 20
<212> TYPE: DNA
<213> ORGANISM: Artificial
<220> FEATURE:
<223> OTHER INFORMATION: Primer KF3
<220> FEATURE:
<221> NAME/KEY: modified_base
<222> LOCATION: (1)..(1)
<223> OTHER INFORMATION: modified with biotin.

<400> SEQUENCE: 98
ataccgatga gtgtgctacc                                            20

<210> SEQ ID NO 99
<211> LENGTH: 42
<212> TYPE: DNA
<213> ORGANISM: Artificial
<220> FEATURE:
<223> OTHER INFORMATION: Primer T36-X-KR3
<220> FEATURE:
<221> NAME/KEY: misc_feature
<222> LOCATION: (22)..(23)
<223> OTHER INFORMATION: g at position 22 is jointed to t at position 23
      by azobenzene represented by Formula (1) of the specification.

<400> SEQUENCE: 99
tactttagag gaaactgctg agtggcctgt gtgacactat gc                   42

<210> SEQ ID NO 100
<211> LENGTH: 27
<212> TYPE: DNA
<213> ORGANISM: Artificial
<220> FEATURE:
<223> OTHER INFORMATION: Probe 37

<400> SEQUENCE: 100
gatcatacac gtggttggaa gctaacc                                    27

<210> SEQ ID NO 101
<211> LENGTH: 25
<212> TYPE: DNA
<213> ORGANISM: Artificial
<220> FEATURE:
<223> OTHER INFORMATION: Probe 38

<400> SEQUENCE: 101
tatgatatgc ttctccacgc ataat                                      25

<210> SEQ ID NO 102
<211> LENGTH: 22
<212> TYPE: DNA

<213> ORGANISM: Artificial
<220> FEATURE:
<223> OTHER INFORMATION: Probe 39

<400> SEQUENCE: 102
ctcagcagtt tcctctaaag ta                                              22

<210> SEQ ID NO 103
<211> LENGTH: 27
<212> TYPE: DNA
<213> ORGANISM: Artificial
<220> FEATURE:
<223> OTHER INFORMATION: Tag sequence T37

<400> SEQUENCE: 103
tggcaacatt tttcactggg tttatag                                         27

<210> SEQ ID NO 104
<211> LENGTH: 27
<212> TYPE: DNA
<213> ORGANISM: Artificial
<220> FEATURE:
<223> OTHER INFORMATION: Tag sequence T38

<400> SEQUENCE: 104
ggttagcttc caaccacgtg tagatca                                         27

<210> SEQ ID NO 105
<211> LENGTH: 20
<212> TYPE: DNA
<213> ORGANISM: Artificial
<220> FEATURE:
<223> OTHER INFORMATION: Primer F

<400> SEQUENCE: 105
ggaaacagct atgaccatga                                                 20

<210> SEQ ID NO 106
<211> LENGTH: 20
<212> TYPE: DNA
<213> ORGANISM: Artificial
<220> FEATURE:
<223> OTHER INFORMATION: Primer R

<400> SEQUENCE: 106
tctatgcggc atcagagcag                                                 20

<210> SEQ ID NO 107
<211> LENGTH: 47
<212> TYPE: DNA
<213> ORGANISM: Artificial
<220> FEATURE:
<223> OTHER INFORMATION: Primer T37-X-F
<220> FEATURE:
<221> NAME/KEY: misc_feature
<222> LOCATION: (27)..(28)
<223> OTHER INFORMATION: g at position 27 is jointed to g at position 28
      by azobenzene represented by Formula (1) of the specification.

<400> SEQUENCE: 107
tggcaacatt tttcactggg tttataggga aacagctatg accatga                   47

<210> SEQ ID NO 108
<211> LENGTH: 47
<212> TYPE: DNA
<213> ORGANISM: Artificial
<220> FEATURE:

```
<223> OTHER INFORMATION: Primer T38-X-R
<220> FEATURE:
<221> NAME/KEY: misc_feature
<222> LOCATION: (27)..(28)
<223> OTHER INFORMATION: a at position 27 is jointed to t at position 28
      by azobenzene represented by Formula (1) of the specification.

<400> SEQUENCE: 108
ggttagcttc caaccacgtg tagatcatct atgcggcatc agagcag                47

<210> SEQ ID NO 109
<211> LENGTH: 27
<212> TYPE: DNA
<213> ORGANISM: Artificial
<220> FEATURE:
<223> OTHER INFORMATION: Probe 40
<220> FEATURE:
<221> NAME/KEY: modified_base
<222> LOCATION: (27)..(27)
<223> OTHER INFORMATION: modified with FITC.

<400> SEQUENCE: 109
ctataaaccc agtgaaaaat gttgcca                                      27

<210> SEQ ID NO 110
<211> LENGTH: 27
<212> TYPE: DNA
<213> ORGANISM: Artificial
<220> FEATURE:
<223> OTHER INFORMATION: Probe 41
<220> FEATURE:
<221> NAME/KEY: modified_base
<222> LOCATION: (27)..(27)
<223> OTHER INFORMATION: modified with biotin.

<400> SEQUENCE: 110
gatcatacac gtggttggaa gctaacc                                      27
```